(12) United States Patent
Karakunnel

(10) Patent No.: US 11,478,479 B2
(45) Date of Patent: Oct. 25, 2022

(54) DOSING WITH AN AZOLOPYRIMIDINE COMPOUND

(71) Applicant: ARCUS BIOSCIENCES, INC., Hayward, CA (US)

(72) Inventor: Joyson Karakunnel, Potomac, MD (US)

(73) Assignee: ARCUS BIOSCIENCES, INC., Hayward, CA (US)

( * ) Notice: Subject to any disclaimer, the term of this patent is extended or adjusted under 35 U.S.C. 154(b) by 119 days.

(21) Appl. No.: 16/970,054

(22) PCT Filed: Feb. 14, 2019

(86) PCT No.: PCT/US2019/018009
§ 371 (c)(1),
(2) Date: Aug. 14, 2020

(87) PCT Pub. No.: WO2019/161054
PCT Pub. Date: Aug. 22, 2019

(65) Prior Publication Data
US 2020/0405718 A1  Dec. 31, 2020

Related U.S. Application Data

(60) Provisional application No. 62/710,394, filed on Feb. 16, 2018.

(51) Int. Cl.
| | | |
|---|---|---|
| A61K 31/506 | (2006.01) | |
| A61P 35/00 | (2006.01) | |
| A61K 33/243 | (2019.01) | |
| A61K 9/20 | (2006.01) | |
| A61K 9/48 | (2006.01) | |
| A61K 31/704 | (2006.01) | |

(52) U.S. Cl.
CPC .............. *A61K 31/506* (2013.01); *A61K 9/20* (2013.01); *A61K 9/48* (2013.01); *A61K 31/704* (2013.01); *A61K 33/243* (2019.01); *A61P 35/00* (2018.01)

(58) Field of Classification Search
CPC ..... A61K 31/506; A61K 31/704; A61P 35/00; C07D 401/14
See application file for complete search history.

(56) References Cited

U.S. PATENT DOCUMENTS

| | | |
|---|---|---|
| 10,399,962 B2 | 9/2019 | Beatty et al. |
| 2013/0053308 A1 | 2/2013 | Camacho Gomez et al. |
| 2013/0289017 A1 | 10/2013 | Dorsch et al. |
| 2018/0215730 A1* | 8/2018 | Beatty ............... A61P 31/00 |
| 2020/0172628 A1* | 6/2020 | Cremasco .......... C07K 16/2896 |

FOREIGN PATENT DOCUMENTS

| | | |
|---|---|---|
| EP | 1439175 A1 | 7/2004 |
| WO | WO-2005058883 A1 | 6/2005 |
| WO | WO-2018136700 | 7/2018 |
| WO | WO-2018152450 A1 | 8/2018 |
| WO | WO-2018182051 A1 | 10/2018 |
| WO | WO-2018183418 A1 | 10/2018 |
| WO | WO-2018183964 A1 | 10/2018 |
| WO | 2019161054 A1 | 8/2019 |

OTHER PUBLICATIONS

Rosen, B.R. et al. "Improved synthesis of sterically encumbered heteroaromatic biaryls from aromatic b-keto esters" Tetrahedron Letters 61 (2020) 151855 (Year: 2020).*
International Search Report for PCT/US2019/018009 dated Apr. 11, 2019, 3 pages.
Ma et al., "Design and synthesis of novel 1,2,3-triazole-pyrimidine hybrids as potential anticancer agents", European Journal of Medicinal Chemistry, Oct. 30, 2014, vol. 86, pp. 368-380; Abstract.
Nagarajan et al., "An eco-friendly mediated synthesis of 1,2,3-triazolyl-2-aminopyrimidine hybrids as highly potent anti-bacterial agents", Chinese Chemical Letters, 2014, vol. 25, pp. 419-422.
Robinson et al., "2-Aminopyrimidines as dual adenosine A1/A2A antagonists", European Journal of Medicinal Chemistry, Nov. 2, 2015, vol. 104, pp. 177-188; Abstract.
Written Opinion of the International Searching Authority for PCT/US2019/018009, dated Apr. 11, 2019, 8 pages.
U.S. Appl. No. 16/460,263, Arcus Biosciences, Inc.
Davari et al., Synthesis and biological evaluation of novel pyridine derivatives as potential anticancer agents and phosphodiesterase-3 inhibitors, Bioorganic Chemistry, 2014, vol. 51, pp. 83-89.
Mitsos, Christos, "Isosteres in Medicinal Chemistry," (Feb. 1, 2006); https://www.scripps.edu/baran/images/grpmtgpdf/Mitsos; 7 pages.
Murugavel et al., Synthesis, Crystal Structure and DFT Studies of 4-(1-Benzyl-5-methyl-1H-1,2,3-triazol-4-yl)-6-(o-tolyl)pyrimidin-2-amine, Asian Journal of Chemistry, 2015, vol. 27, No. 3, pp. 074-978.
Dong et al., Tandem Michael Addition/Imino-Nitrile Cyclization Synthesis of 2-Amino-6-(1-aryl-5-methyl-1H-1,2,3-triazol-4yl)-4-phenylpyridine-3-carbonitrile. J. Heterocyclic Chem., 47, 389 (2010). 7 pages.

(Continued)

*Primary Examiner* — Andrew S Rosenthal
(74) *Attorney, Agent, or Firm* — Sheppard Mullin Richter & Hampton LLP

(57) ABSTRACT

Provided herein are methods of treating a disease, disorder, or condition, mediated at least in part by the adenosine $A_{2A}$ N receptor ($A_{2A}R$) and/or the adenosine $A_{2B}$ receptor ($A_{2B}R$) using Compound (I). In some embodiments, the disease or disorder is a cancer related disorder. Also provided herein are pharmaceutical compositions and single unit dosages of Compound (I).

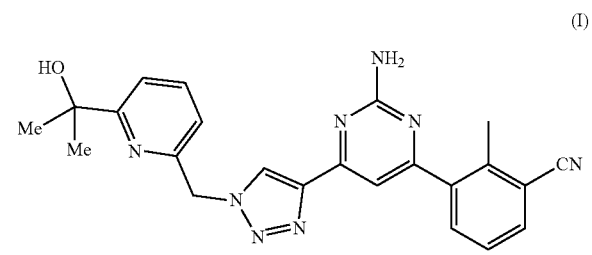

(I)

25 Claims, 4 Drawing Sheets

(56) References Cited

OTHER PUBLICATIONS

Examination Report for Indian Patent Application No. 202017039301 dated Feb. 21, 2022. 5 pages.
Extended European Search Report for European Patent Application No. 19754719.3 dated Oct. 14, 2021. 11 pages.
Vijayan et al., Targeting immunosuppressive adenosine in cancer. Nature Reviews Cancer 2017; vol. 17, pp. 709-724. XP055557876.
Walters et al., 32nd Annual Meeting and Pre-Conference Programs of the Society for Immunotherapy of Cancer (SITC 2017): Part Two. National Harbor, MD, USA. Nov. 8-12, 2017. Journal for ImmunoTherapy of Cancer 2017, 5(Suppl 2):87, DOI 10.1186/S40425-017-0288-4, Abstract p. 498, p. 240/244. XP055846682.
Walters et al., Abstract 4572: Characterization of the potent and selective A2aR antagonist AB928 for the treatment of cancer. Cancer Research 2017, vol. 77 (13 Supplement): pp. 1-4. XP055846686.

\* cited by examiner

DOSING WITH AN AZOLOPYRIMIDINE COMPOUND

CROSS-REFERENCES TO RELATED APPLICATIONS

This application is an application claiming priority benefit under 35 U.S.C. § 119(e) of U.S. Provisional Application No. 62/710,394 filed Feb. 16, 2018, which is herein incorporated by reference in its entirety for all purposes.

STATEMENT AS TO RIGHTS TO INVENTIONS MADE UNDER FEDERALLY SPONSORED RESEARCH AND DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK

NOT APPLICABLE

BACKGROUND OF THE INVENTION

Adenosine is a purine nucleoside compound comprising a complex of adenine and a ribose sugar molecule (ribofuranose). It is mainly generated extracellularly by the sequential enzymatic cleavage of adenosine triphosphate (ATP) to adenosine monophosphate (AMP) by CD39 ectonucleotidase and AMP (to adenosine) by CD73 ectonucleotidase (Borea et al, Br J Pharmacol. 2017; 174:1945-1960; Chen et al, Nat Rev Drug Discov. 2013; 12:265-286). Adenosine may be transported between the extracellular and intracellular compartments via the equilibrative nucleoside transporter 1 (ENT-1). If adenosine accumulates extracellularly, adenosine will act on several adenosine receptors, including $A_1R$, $A_{2a}R$, $A_{2b}R$, and $A_3R$ (Schmidt and Ferk, J Pharm Pharmacol. 2017; 69:790-806).

$A_{2a}R$ signaling has been well characterized in tumor mouse models. Genetic deletion of $A_{2a}R$ in mice leads to increased rejection of immunogenic tumors, and $A_{2a}R$-deficient mice were protected from EL4 thymoma tumor growth. Cancer cells that express CD73 are more prone to metastasis when $A_{2a}R$ is activated, $A_{2a}R$-deficient mice were protected from metastasis, and $A_{2a}R$ blockade led to inhibition of tumor growth and metastasis (Beavis et al, Cancer immunol Res. 2015; 3:506-517; Ohta et al, Proc Natl Acad Sci USA. 2006; 103:13132-13137; Waickman et al, Cancer Immunol Immunother. 2012; 61:917-926).

$A_{2b}R$ activation has been shown to be tumorigenic in mouse models. $A_{2b}R$, which is expressed in prostate cancer cell lines, leads to decreases in chemotherapy-induced cell death when activated (Wei et al, J Immunol. 2013; 190:138-146). MDA-MB-231 cells have shown in vitro proliferation and migration with $A_{2b}R$ activation (Fernandez et al, PLoS ONE. 2016; 11:e0167445). In mice bearing MB49 and 4T1 tumors, blockade of $A_{2b}R$ resulted in a reduction in breast tumor growth and lung metastasis (Cekic et al, J Immunol. 2012; 188:198-205).

Adenosine serves in processes associated with vasodilation, including cardiac vasodilation, and acts as a neuromodulator (e.g., it is thought to be involved in promoting sleep). In addition to its involvement in these biochemical processes, adenosine is used as a therapeutic antiarrhythmic agent to treat, for example, supraventricular tachycardia. As discussed herein, tumors evade host responses by inhibiting immune function and promoting tolerance, and adenosine has been shown to play an important role in mediating tumor evasion of the immune system. Adenosine signaling through $A_{2A}Rs$ and $A_{2B}Rs$, expressed on a variety of immune cell subsets and endothelial cells, has been established as having an important role in protecting tissues during inflammatory responses. As such, under certain conditions adenosine protects tumors from immune destruction (see, e.g., Fishman, P, et al. (2009) Handb Exp Pharmacol 193:399-441).

Historically, modulators of adenosine receptors have been nonselective. This is acceptable in certain indications, such as where the endogenous agonist adenosine, which acts on all four adenosine receptors in cardiac tissue, is administered parenterally for the treatment of severe tachycardia. However, the use of sub-type selective adenosine receptor agonists and antagonists provides the potential for achieving desired outcomes while minimizing or eliminating adverse effects.

Despite advancements in the understanding adenosine receptor pathways and the targeting of particular adenosine receptor subtypes, proper dosing to maximize efficacy while minimizing undesirable side-effects are not known.

As such, there is a need in the art for methods for administering sub-type selective adenosine receptor agonists. The present disclosure addresses this need and provides related advantages as well.

BRIEF SUMMARY OF THE INVENTION

The present disclosure relates to the use of Compound I for the treatment and/or prevention of a diverse array of diseases, disorders and conditions mediated, in whole or in part, by the adenosine $A_{2A}$ receptor ($A_{2A}R$) and/or the adenosine $A_{2B}$ receptor ($A_{2B}R$). Such diseases, disorders and conditions are described in detail elsewhere herein. Said use includes administering a total daily dosage of about 5 to 250 mg of Compound I or a pharmaceutically acceptable salt thereof.

As discussed hereafter, although the compounds of the present invention are believed to effect their activity by inhibition the adenosine $A_{2A}$ receptor ($A_{2A}R$) and the adenosine $A_{2B}$ receptor ($A_{2B}R$), a precise understanding of the compounds' underlying mechanism of action is not required to practice the invention. It is envisaged that the compounds may alternatively effect their activity through direct or indirect inhibition of adenylyl cyclase. It is also envisaged that the compounds may effect their activity through inhibition of both $A_{2A}$ receptor ($A_{2A}R$) and the adenosine $A_{2B}$ receptor ($A_{2B}R$) as well as adenylyl cyclase. Although the compounds of the invention are generally referred to herein as adenosine $A_{2A}$ receptor ($A_{2A}R$) and adenosine $A_{2B}$ receptor ($A_{2B}R$) inhibitors, it is to be understood that the term "$A_{2A}R/A_{2B}R$ inhibitors" encompasses compounds that act individually through inhibition of $A_{2A}R$, $A_{2B}R$ or adenylyl cyclase, and/or compounds that act through inhibition of $A_{2A}R$, $A_{2B}R$, and adenylyl cyclase.

The $A_{2A}$ and $A_{2B}$ cell surface adenosine receptors are found to be upregulated in various tumor cells. Thus, antagonists of the $A_{2A}$ and $A_{2B}$ adenosine receptors such as Compound I represent a promising oncology therapeutic.

Activation of the $A_{2A}$ adenosine receptor results in inhibition of the immune response to tumors via suppression of T regulatory cell function and inhibition of natural killer cell cytotoxicity and tumor-specific CD4+/CD8+ activity. Therefore, inhibition of this receptor subtype by specific antagonists may enhance immunotherapeutics in cancer therapy.

Activation of the $A_{2B}$ adenosine receptor plays a role in the development of tumors via upregulation of the expression levels of angiogenic factors in microvascular endothelial cells. [See, e.g., P. Fishman et al., Handb Exp Pharmacol (2009); 193:399-441]. Moreover, adenosine receptor 2A blockade has been shown to increase the efficacy of anti-PD-1 through enhanced anti-tumor T cell responses (P. Beavis, et al., Cancer Immunol Res DOI: 10.1158/2326-6066.CIR-14-0211 Published 11 Feb. 2015). A more comprehensive discussion of the roles of the $A_{2A}$Rs and the $A_{2B}$Rs is set forth hereafter.

Adenosine 2A Receptor ($A_{2A}$R)

The $A_{2A}$R (also referred to as ADORA2A) is a G protein-coupled receptor (GPCR), family members of which possess seven transmembrane alpha helices. Based on its crystallographic structure, the $A_{2A}$R comprises a ligand binding pocket distinct from that of other structurally determined GPCRs (e.g., the beta-2 adrenergic receptor).

As set forth elsewhere herein, adenosine is involved in mediating tumor evasion of the immune system. The $A_{2A}$R plays a critical, nonredundant role in mediating adenosine-induced anti-inflammatory responses. The $A_{2A}$R negatively regulates immune responses, and thus pharmacologic inhibition of $A_{2A}$R activation has been demonstrated to be a viable means of enhancing immunotherapy.

As noted above, activation of the $A_{2A}$R impacts the adaptive immune response; by way of example, the $A_{2A}$R protects the host from excessive tissue destruction by not only acutely inhibiting T-cell function, but by also promoting the development of regulatory T cells. Because $A_{2A}$R activation is a potent inhibitor of adaptive immune responses, tumor-derived adenosine has been implicated in blocking antitumor immunity.

In addition to its other roles, the $A_{2A}$R has been implicated in selectively enhancing anti-inflammatory cytokines, promoting the upregulation of PD-1 and CTLA-4, promoting the generation of LAG-3 and Foxp3+ regulatory T cells, and mediating the inhibition of regulatory T cells. PD-1, CTLA-4 and other immune checkpoints are discussed further herein. As all of these immunosuppressive properties have been identified as mechanisms by which tumors evade host responses, a cancer immunotherapeutic regimen that includes an $A_{2A}$R antagonist may result in enhanced tumor immunotherapy. [See generally, Naganuma, M., et al. (2006) J Immunol 177:2765-769].

$A_{2A}$R antagonists likely play an important role in chemotherapy and radiation therapy. Mechanistically, the concomitant administration of $A_{2A}$R antagonists during chemotherapy or radiation therapy has been proposed to lead to the expansion of tumor-specific T cells while simultaneously preventing the induction of tumor-specific regulatory T cells. Furthermore, combining $A_{2A}$R antagonists with tumor vaccines is thought to provide at least an additive effect in view of their divergent mechanisms of action. Finally, $A_{2A}$R antagonists may most effectively be used in combination with tumor vaccines and other checkpoint blockers. By way of example, blocking PD-1 engagement as well as inhibiting the $A_{2A}$R might mitigate the ability of tumors to turn off tumor-specific effector T cells (see, e.g., Fishman, P, et al. (2009) Handb Exp Pharmacol 193:399-441). Moreover, adenosine signaling through the $A_{2A}$R receptor has been found to be a promising negative feedback loop, and preclinical studies have confirmed that blockade of $A_{2A}$R activation can markedly enhance anti-tumor immunity (Sitkovsky, M V, et al. (2014) Cancer Immun Res 2:598-605).

Adenosine 2B Receptor ($A_{2B}$R)

The $A_{2B}$R (also referred to as ADORA2B) is a GPCR found in many different cell types. It requires higher concentrations of adenosine for activation than other adenosine receptor subtypes (e.g., $A_1$R, $A_{2A}$R, and $A_3$R) (Fredholm B B, et al. (2001) Biochem Pharmacol 61:443-448). Such conditions have been seen in, for example, tumors where hypoxia is commonly observed. Contrary to the other adenosine receptor subtypes, the $A_{2B}$R may play an important role in pathophysiological conditions associated with massive adenosine release. Thus, selective blockade or stimulation of this adenosine receptor subtype may not interfere with the numerous important physiological functions of adenosine mediated via other adenosine receptor subtypes. However, the pathway leading to $A_{2B}$R-mediated inhibition is not fully understood.

Angiogenesis represents a pivotal mechanism for tumor growth. The angiogenesis process is highly regulated by an array of angiogenic factors and is triggered by adenosine under particular circumstances that are associated with hypoxia. The $A_{2B}$R is expressed in human microvascular endothelial cells, where it plays an important role in the regulation of the expression of angiogenic factors such as vascular endothelial growth factor (VEGF). In certain tumor types, hypoxia has been observed to cause an upregulation of $A_{2B}$Rs, suggesting that $A_{2B}$Rs play a critical role in mediating the effects of adenosine on angiogenesis. Thus, blockade of $A_{2B}$Rs may limit tumor growth by limiting the oxygen supply to the tumor cells. Furthermore, experiments involving adenylate cyclase activation indicate that $A_{2B}$Rs are the sole adenosine receptor subtype in certain tumor cells, suggesting that $A_{2B}$R antagonists may exhibit effects on particular tumor types (see, e.g., Feoktistov, I. et al. (2003) Circ Res 92:485-492).

Recent data complicate an understanding of the precise role of $A_{2B}$R modulators. As discussed above, data confirm that $A_{2B}$Rs play an important role in mediating the effects of adenosine on tumor growth and progression. Indeed, inhibition of angiogenesis and inhibition of ERK 1/2 phosphorylation represent the most interesting effects for a potential anticancer treatment based on $A_{2B}$R as a target. However, while inhibition of angiogenesis requires the use of $A_{2B}$R antagonists, inhibition of growth signaling via other clinically relevant pathways (e.g., the MAP kinase pathway) might be achieved through treatment with $A_{2B}$R agonists (see, e.g., Graham, S. et al. (2001) Eur J Pharmaol 420:19-26). The results of additional experimentation may indicate that both agonists and antagonists will provide useful options for treatment in combination with other therapeutic measures if used at different stages of the disease and its treatment.

In some embodiments, the present disclosure contemplates methods for treating or preventing cancer in a subject (e.g., a human) comprising administering to the subject a therapeutically effective amount of Compound I. In some embodiments, the present invention includes methods of treating or preventing a cancer in a subject by administering to the subject Compound I in an amount effective to reverse or stop the progression of $A_{2A}$R-mediated immunosuppression. In some embodiments, the total daily dosage of Compound I administered to said individual is about 5 to 250 mg. In some embodiments, the total daily dosage of Compound I administered to said individual is about 75 to 150 mg. In some embodiments, the total daily dosage of Compound I administered to said individual is about 75 mg. In some embodiments, the total daily dosage of Compound I administered to said individual is about 100 mg. In some embodiments, the total daily dosage of Compound I administered to said individual is about 150 mg. In some embodiments, the $A_{2A}R$-mediated immunosuppression is mediated by an antigen-presenting cell (APC).

Examples of the cancers that may be treated using the compounds and compositions described herein include, but are not limited to: cancers of the prostate, colorectum, pancreas, cervix, stomach, endometrium, brain, liver, bladder, ovary, testis, head, neck, skin (including melanoma and basal carcinoma), mesothelial lining, white blood cell (including lymphoma and leukemia) esophagus, breast, muscle, connective tissue, lung (including small-cell lung carcinoma and non-small-cell carcinoma), adrenal gland, thyroid, kidney, or bone; glioblastoma, mesothelioma, renal cell carcinoma, gastric carcinoma, sarcoma, choriocarcinoma, cutaneous basocellular carcinoma, and testicular seminoma. In some embodiments of the present invention, the cancer is melanoma, colon cancer, pancreatic cancer, breast cancer, prostate cancer, lung cancer, leukemia, a brain tumor, lymphoma, sarcoma, ovarian cancer, head and neck cancer, cervical cancer or Kaposi's sarcoma. Cancers that are candidates for treatment with the compounds and compositions of the present invention are discussed further hereafter.

In still other embodiments, the present invention contemplates methods for treating or preventing an immune-related disease, disorder or condition in a subject (e.g., a human), comprising administering to the subject a total daily dosage of about 5 to 250 mg of Compound I. Examples of immune-related diseases, disorders and conditions are described hereafter. In some embodiments, the total daily dosage of Compound I administered to said individual is about 75 to 150 mg. In some embodiments, the total daily dosage of Compound I administered to said individual is about 75 mg. In some embodiments, the total daily dosage of Compound I is about 100 mg. In some embodiments, the total daily dosage of Compound I administered to said individual is about 150 mg.

Other diseases, disorders and conditions that can be treated or prevented, in whole or in part, by modulation of $A_{2A}R/A_{2B}R$ activity are candidate indications for Compound I.

The present invention further contemplates the use of Compound I in combination with one or more additional agents. The one or more additional agents may have some adenosine $A_{2A}$ receptor and/or adenosine $A_{2B}$ receptor modulating activity; alternatively, they may function through distinct mechanisms of action. In some embodiments, such agents comprise radiation (e.g., localized radiation therapy or total body radiation therapy) and/or other treatment modalities of a non-pharmacological nature. When combination therapy is utilized, the compound(s) described herein and the one additional agent(s) may be in the form of a single composition or multiple compositions, and the treatment modalities may be administered concurrently, sequentially, or through some other regimen. By way of example, the present invention contemplates a treatment regimen wherein a radiation phase is followed by a chemotherapeutic phase. The combination therapy may have an additive or synergistic effect. Other benefits of combination therapy are described hereafter.

In particular embodiments, the present invention contemplates the use of Compound I in combination with immune checkpoint inhibitors. The blockade of immune checkpoints, which results in the amplification of antigen-specific T cell responses, has been shown to be a promising approach in human cancer therapeutics. Examples of immune checkpoints (ligands and receptors), some of which are selectively upregulated in various types of tumor cells, that are candidates for blockade include PD1 (programmed cell death protein 1); PDL1 (PD1 ligand); BTLA (B and T lymphocyte attenuator); CTLA4 (cytotoxic T-lymphocyte associated antigen 4); TIGIT (T cell immunoreceptor with Ig and ITIM domains); TIM3 (T-cell membrane protein 3); LAG3 (lymphocyte activation gene 3); and Killer Inhibitory Receptors. Immune checkpoint inhibitors, and combination therapy therewith, are discussed in detail elsewhere herein.

In other embodiments, the present invention provides methods for treating cancer in a subject, comprising administering to the subject a total daily dosage of 5 to 250 mg of Compound I and at least one chemotherapeutic agent, such agents including, but not limited to alkylating agents (e.g., nitrogen mustards such as chlorambucil, cyclophosphamide, isofamide, mechlorethamine, melphalan, and uracil mustard; aziridines such as thiotepa; methanesulphonate esters such as busulfan; nucleoside analogs (e.g., gemcitabine); nitroso ureas such as carmustine, lomustine, and streptozocin; topoisomerase 1 inhibitors (e.g., irinotecan); platinum complexes such as cisplatin, oxaplatin, and carboplatin; bioreductive alkylators such as mitomycin, procarbazine, dacarbazine and altretamine); DNA strand-breakage agents (e.g., bleomycin); topoisomerase II inhibitors (e.g., amsacrine, dactinomycin, daunorubicin, idarubicin, mitoxantrone, doxorubicin, etoposide, and teniposide); DNA minor groove binding agents (e.g., plicamydin); antimetabolites (e.g., folate antagonists such as methotrexate and trimetrexate; pyrimidine antagonists such as fluorouracil, fluorodeoxyuridine, CB3717, azacitidine, cytarabine, and floxuridine; purine antagonists such as mercaptopurine, 6-thioguanine, fludarabine, pentostatin; asparginase; and ribonucleotide reductase inhibitors such as hydroxyurea); tubulin interactive agents (e.g., vincristine, estramustine, vinblastine, docetaxol, epothilone derivatives, and paclitaxel); hormonal agents (e.g., estrogens; conjugated estrogens; ethinyl estradiol; diethylstilbesterol; chlortrianisen; idenestrol; progestins such as hydroxyprogesterone caproate, medroxyprogesterone, and megestrol; and androgens such as testosterone, testosterone propionate, fluoxymesterone, and methyltestosterone); adrenal corticosteroids (e.g., prednisone, dexamethasone, methylprednisolone, and prednisolone); leutinizing hormone releasing agents or gonadotropin-releasing hormone antagonists (e.g., leuprolide acetate and goserelin acetate); and antihormonal antigens (e.g., tamoxifen, antiandrogen agents such as flutamide; and antiadrenal agents such as mitotane and aminoglutethimide). The present invention also contemplates the use of Compound I in combination with other agents known in the art (e.g., arsenic trioxide) and other chemotherapeutic agents developed in the future.

In some embodiments drawn to methods of treating cancer, the administration of a total daily dosage of about 5 to 250 mg of Compound I with at least one chemotherapeutic agent results in a cancer survival rate greater than the cancer survival rate observed by administering either alone. In further embodiments drawn to methods of treating cancer, the administration of a total daily dosage of about 5 to 250 mg of Compound I in combination with at least one chemotherapeutic agent results in a reduction of tumor size or a slowing of tumor growth greater than reduction of the tumor size or tumor growth observed by administration of one agent alone.

In further embodiments, the present invention contemplates methods for treating or preventing cancer in a subject, comprising administering to the subject a total daily dosage of about 5 to 250 mg of Compound I and at least one signal transduction inhibitor (STI). In a particular embodiment, the at least one STI is selected from the group consisting of bcr/abl kinase inhibitors, epidermal growth factor (EGF) receptor inhibitors, her-2/neu receptor inhibitors, and farnesyl transferase inhibitors (FTIs). Other candidate STI agents are set forth elsewhere herein.

The present invention also contemplates methods of augmenting the rejection of tumor cells in a subject comprising administering a total daily dosage of about 5 to 250 mg of Compound I in conjunction with at least one chemotherapeutic agent and/or radiation therapy, wherein the resulting rejection of tumor cells is greater than that obtained by administering either Compound I, the chemotherapeutic agent or the radiation therapy alone.

In further embodiments, the present invention provides methods for treating cancer in a subject, comprising administering to the subject a total daily dosage of about 5 to 250 mg of Compound I and at least one immunomodulator other than an $A_{2A}R/A_{2B}R$ inhibitors. In particular embodiments, the at least one immunomodulator is selected from the group consisting of CD4OL, B7, B7RP1, anti-CD40, anti-CD38, anti-ICOS, 4-IBB ligand, dendritic cell cancer vaccine, IL2, IL12, ELC/CCL19, SLC/CCL21, MCP-1, IL-4, IL-18, TNF, IL-15, MDC, IFN-a/-13, M-CSF, IL-3, GM-CSF, IL-13, and anti-IL-10. Other candidate immunomodulator agents are set forth elsewhere herein.

The present invention contemplates embodiments comprising methods for treating or preventing an infective disorder (e.g., a viral infection) in a subject (e.g., a human) comprising administering to the subject a total daily dosage of 5 to 250 mg of Compound I and a therapeutically effective amount of an anti-infective agent(s).

In some embodiments of the present invention, the additional therapeutic agent is a cytokine, including, for example granulocyte-macrophage colony stimulating factor (GM-CSF) or flt3-ligand. The present invention also contemplates methods for treating or preventing a viral infection (e.g., a chronic viral infection) including, but not limited to, hepatitis C virus (HCV), human papilloma virus (HPV), cytomegalovirus (CMV), Epstein-Barr virus (EBV), varicella zoster virus, coxsackie virus, and human immunodeficiency virus (HIV). The use of the compounds described herein to treat (either alone or as a component of combination therapy) infection is discussed further hereafter.

In additional embodiments, treatment of an infective disorder is effected through the co-administration of a vaccine in combination with administration of a total daily dosage of 5 to 250 mg of Compound I. In some embodiments, the vaccine is an anti-viral vaccine, including, for example, an anti-HIV vaccine. In other embodiments, the vaccine is effective against tuberculosis or malaria. In still other embodiments, the vaccine is a tumor vaccine (e.g., a vaccine effective against melanoma); the tumor vaccine may comprise genetically modified tumor cells or a genetically modified cell line, including genetically modified tumor cells or a genetically modified cell line that has been transfected to express granulocyte-macrophage stimulating factor (GM-C SF). In particular embodiments, the vaccine includes one or more immunogenic peptides and/or dendritic cells.

In some embodiments, the present invention contemplates methods of using the compounds described herein in combination with one or more antimicrobial agents.

In certain embodiments drawn to treatment of an infection by administering a total daily dosage of 5 to 250 mg of Compound I and at least one additional therapeutic agent, a symptom of infection observed after administering both Compound I and the additional therapeutic agent is improved over the same symptom of infection observed after administering either alone. In some embodiments, the symptom of infection observed can be reduction in viral load, increase in $CD4^+$ T cell count, decrease in opportunistic infections, increased survival time, eradication of chronic infection, or a combination thereof.

DETAILED DESCRIPTION OF THE INVENTION

Figure 1:
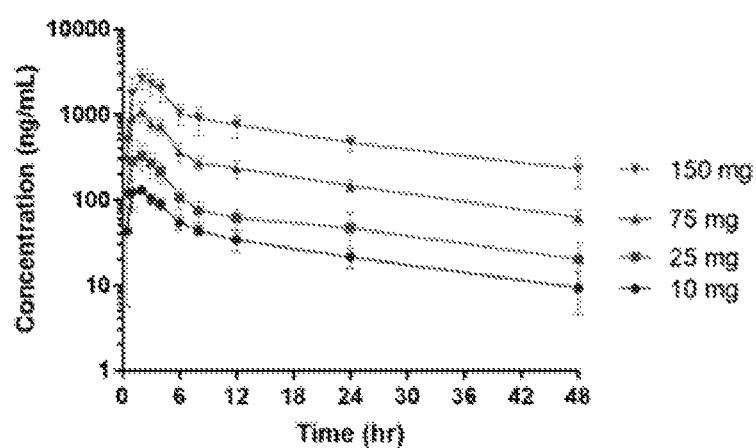
FIG. 1 shows the measured plasma concentration-time profiles on semi-logarithmic scale of Compound I administered to humans at 10 mg, 25 mg, 75 mg, and 150 mg.

Before the present invention is further described, it is to be understood that the invention is not limited to the particular embodiments set forth herein, and it is also to be understood that the terminology used herein is for the purpose of describing particular embodiments only, and is not intended to be limiting.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention. Unless defined otherwise, all technical and scientific terms used herein have the same meaning as commonly understood by one of ordinary skill in the art to which this invention belongs.

As used herein, the singular forms "a," "an," and "the" include plural referents unless the context clearly dictates otherwise. It is further noted that the claims may be drafted to exclude any optional element. As such, this statement is intended to serve as antecedent basis for use of such exclusive terminology such as "solely," "only" and the like in connection with the recitation of claim elements, or use of a "negative" limitation.

The publications discussed herein are provided solely for their disclosure prior to the filing date of the present application. Further, the dates of publication provided may be different from the actual publication dates, which may need to be independently confirmed.

General

The present disclosure provides, inter alia, methods of treating a disease, disorder, or condition, mediated at least in part by the adenosine $A_{2A}$ receptor ($A_{2A}R$) or the adenosine $A_{2B}$ receptor ($A_{2B}R$) by administering to a subject in need thereof a total daily dosage of about 5 to 250 mg of Compound I, having the formula

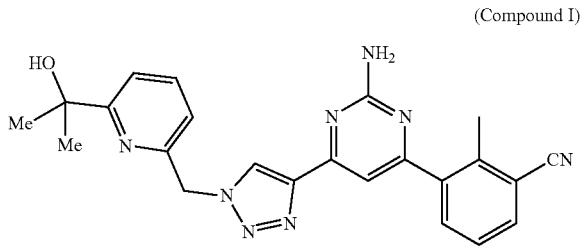 [SMILES: Cc1c(C#N)cccc1-c1cc(-c2cn(Cc3cccc(C(C)(C)O)n3)nn2)nc(N)n1]

(Compound I)

or a pharmaceutically acceptable salt thereof.

Compound I is a dual inhibitor of the $A_{2a}R$ and $A_{2b}R$ receptors and is a particularly useful compound because it provides (i) significant potency under conditions that closely resemble the tumor microenvironment, for example, high concentrations of adenosine and albumin, (ii) low penetration through the blood-brain barrier, (iii) high penetration of tumor tissue and (iv) attractive pharmacokinetics, with high oral bioavailability and a human half-life that enables once-daily dosing.

As mentioned above, Compound I provides low penetration through the blood-brain barrier. Without being bound to any particular theory, it is believed that this property will allow higher dosing levels before the appearance of adverse events associate with inhibition of the $A_{2a}R$ receptor in the brain. Furthermore, it is believed that a dual antagonist that binds $A_{2a}R$ and $A_{2b}R$ will have broader immunological and anti-tumor activity over known non-specific compounds and selective antagonists that only target a singe receptor.

Definitions

Unless otherwise indicated, the following terms are intended to have the meaning set forth below. Other terms are defined elsewhere throughout the specification.

"Compound I" refers to the chemical 3-(2-amino-6-(1-((6-(2-hydroxypropan-2-yl)pyridin-2-yl)methyl)-1H-1,2,3-triazol-4-yl)pyrimidin-4-yl)-2-methylbenzonitrile, having the formula:

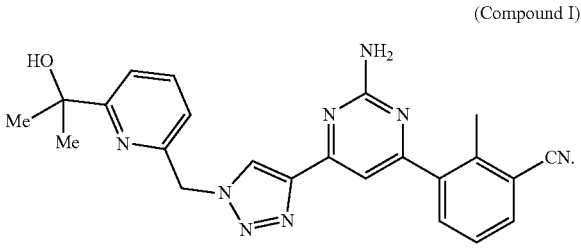 [SMILES: Cc1c(C#N)cccc1-c1cc(-c2cn(Cc3cccc(C(C)(C)O)n3)nn2)nc(N)n1]

(Compound I)

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galacturonic acids and the like (see, for example, Berge, S. M., et al, "Pharmaceutical Salts", *Journal of Pharmaceutical Science*, 1977, 66, 1-19). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention. In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent. Prodrugs are described in more detail elsewhere herein.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers, regioisomers and individual isomers (e.g., separate enantiomers) are all intended to be encompassed within the scope of the present invention. When a stereochemical depiction is shown, it is meant to refer the compound in which one of the isomers is present and substantially free of the other isomer. 'Substantially free of' another isomer indicates at least an 80/20 ratio of the two isomers, more preferably 90/10, or 95/5 or more. In some embodiments, one of the isomers will be present in an amount of at least 99%.

The compounds of the present invention may also contain unnatural proportions of atomic isotopes at one or more of the atoms that constitute such compounds. Unnatural proportions of an isotope may be defined as ranging from the amount found in nature to an amount consisting of 100% of the atom in question. For example, the compounds may incorporate radioactive isotopes, such as for example tritium ($^3$H), iodine-125 ($^{125}$I) or carbon-14 ($^{14}$C), or non-radioactive isotopes, such as deuterium ($^2$H) or carbon-13 ($^{13}$C). Such isotopic variations can provide additional utilities to those described elsewhere within this application. For instance, isotopic variants of the compounds of the invention may find additional utility, including but not limited to, as diagnostic and/or imaging reagents, or as cytotoxic/radiotoxic therapeutic agents. Additionally, isotopic variants of the compounds of the invention can have altered pharmacokinetic and pharmacodynamic characteristics which can contribute to enhanced safety, tolerability or efficacy during treatment. All isotopic variations of the compounds of the present invention, whether radioactive or not, are intended to be encompassed within the scope of the present invention.

The terms "patient" or "subject" are used interchangeably to refer to a human or a non-human animal (e.g., a mammal).

The terms "administration", "administer" and the like, as they apply to, for example, a subject, cell, tissue, organ, or biological fluid, refer to contact of, for example, an inhibitor of $A_{2A}R/A_{2B}R$, a pharmaceutical composition comprising same, or a diagnostic agent to the subject, cell, tissue, organ, or biological fluid. In the context of a cell, administration includes contact (e.g., in vitro or ex vivo) of a reagent to the cell, as well as contact of a reagent to a fluid, where the fluid is in contact with the cell.

The terms "treat", "treating", treatment" and the like refer to a course of action (such as administering an inhibitor of $A_{2A}R/A_{2B}R$ or a pharmaceutical composition comprising same) initiated after a disease, disorder or condition, or a symptom thereof, has been diagnosed, observed, and the like so as to eliminate, reduce, suppress, mitigate, or ameliorate, either temporarily or permanently, at least one of the underlying causes of a disease, disorder, or condition afflicting a subject, or at least one of the symptoms associated with a disease, disorder, condition afflicting a subject. Thus, treatment includes inhibiting (e.g., arresting the development or further development of the disease, disorder or condition or clinical symptoms association therewith) an active disease.

The term "in need of treatment" as used herein refers to a judgment made by a physician or other caregiver that a subject requires or will benefit from treatment. This judgment is made based on a variety of factors that are in the realm of the physician's or caregiver's expertise.

The terms "prevent", "preventing", "prevention" and the like refer to a course of action (such as administering Compound I or a pharmaceutical composition comprising same) initiated in a manner (e.g., prior to the onset of a disease, disorder, condition or symptom thereof) so as to prevent, suppress, inhibit or reduce, either temporarily or permanently, a subject's risk of developing a disease, disorder, condition or the like (as determined by, for example, the absence of clinical symptoms) or delaying the onset thereof, generally in the context of a subject predisposed to having a particular disease, disorder or condition. In certain instances, the terms also refer to slowing the progression of the disease, disorder or condition or inhibiting progression thereof to a harmful or otherwise undesired state.

The term "in need of prevention" as used herein refers to a judgment made by a physician or other caregiver that a subject requires or will benefit from preventative care. This judgment is made based on a variety of factors that are in the realm of a physician's or caregiver's expertise.

The phrase "therapeutically effective amount" refers to the administration of an agent to a subject, either alone or as part of a pharmaceutical composition and either in a single dose or as part of a series of doses, in an amount capable of having any detectable, positive effect on any symptom, aspect, or characteristic of a disease, disorder or condition when administered to the subject. The therapeutically effective amount can be ascertained by measuring relevant physiological effects, and it can be adjusted in connection with the dosing regimen and diagnostic analysis of the subject's condition, and the like. By way of example, measurement of the serum level of an $A_{2A}R/A_{2B}R$ inhibitor (or, e.g., a metabolite thereof) at a particular time post-administration may be indicative of whether a therapeutically effective amount has been used.

The phrase "in a sufficient amount to effect a change" means that there is a detectable difference between a level of an indicator measured before (e.g., a baseline level) and after administration of a particular therapy. Indicators include any objective parameter (e.g., serum concentration) or subjective parameter (e.g., a subject's feeling of well-being).

The term "small molecules" refers to chemical compounds having a molecular weight that is less than about 10 kDa, less than about 2 kDa, or less than about 1 kDa. Small molecules include, but are not limited to, inorganic molecules, organic molecules, organic molecules containing an inorganic component, molecules comprising a radioactive atom, and synthetic molecules. Therapeutically, a small molecule may be more permeable to cells, less susceptible to degradation, and less likely to elicit an immune response than large molecules.

The term "ligand" refers to, for example, a peptide, a polypeptide, a membrane-associated or membrane-bound molecule, or a complex thereof, that can act as an agonist or antagonist of a receptor. A ligand encompasses natural and synthetic ligands, e.g., cytokines, cytokine variants, analogs, muteins, and binding compositions derived from antibodies, as well as small molecules. The term also encompasses an agent that is neither an agonist nor antagonist, but that can bind to a receptor without significantly influencing its biological properties, e.g., signaling or adhesion. Moreover, the term includes a membrane-bound ligand that has been changed by, e.g., chemical or recombinant methods, to a soluble version of the membrane-bound ligand. A ligand or receptor may be entirely intracellular, that is, it may reside in the cytosol, nucleus, or some other intracellular compartment. The complex of a ligand and receptor is termed a "ligand-receptor complex."

The terms "inhibitors" and "antagonists", or "activators" and "agonists" refer to inhibitory or activating molecules, respectively, for example, for the activation of, e.g., a ligand, receptor, cofactor, gene, cell, tissue, or organ. Inhibitors are molecules that decrease, block, prevent, delay activation, inactivate, desensitize, or down-regulate, e.g., a gene, protein, ligand, receptor, or cell. Activators are molecules that increase, activate, facilitate, enhance activation, sensitize, or up-regulate, e.g., a gene, protein, ligand, receptor, or cell. An inhibitor may also be defined as a molecule that reduces, blocks, or inactivates a constitutive activity. An "agonist" is a molecule that interacts with a target to cause or promote an increase in the activation of the target. An "antagonist" is a molecule that opposes the action(s) of an agonist. An antagonist prevents, reduces, inhibits, or neutralizes the activity of an agonist, and an antagonist can also prevent, inhibit, or reduce constitutive activity of a target, e.g., a target receptor, even where there is no identified agonist.

The terms "modulate", "modulation" and the like refer to the ability of a molecule (e.g., an activator or an inhibitor) to increase or decrease the function or activity of $A_{2A}R/A_{2B}R$, either directly or indirectly. A modulator may act alone, or it may use a cofactor, e.g., a protein, metal ion, or small molecule. Examples of modulators include small molecule compounds and other bioorganic molecules. Numerous libraries of small molecule compounds (e.g., combinatorial libraries) are commercially available and can serve as a starting point for identifying a modulator. The skilled artisan is able to develop one or more assays (e.g., biochemical or cell-based assays) in which such compound libraries can be screened in order to identify one or more compounds having the desired properties; thereafter, the skilled medicinal chemist is able to optimize such one or more compounds by, for example, synthesizing and evaluating analogs and derivatives thereof. Synthetic and/or molecular modeling studies can also be utilized in the identification of an Activator.

The "activity" of a molecule may describe or refer to the binding of the molecule to a ligand or to a receptor; to catalytic activity; to the ability to stimulate gene expression or cell signaling, differentiation, or maturation; to antigenic activity; to the modulation of activities of other molecules; and the like. The term "proliferative activity" encompasses an activity that promotes, that is necessary for, or that is specifically associated with, for example, normal cell division, as well as cancer, tumors, dysplasia, cell transformation, metastasis, and angiogenesis.

As used herein, "comparable", "comparable activity", "activity comparable to", "comparable effect", "effect comparable to", and the like are relative terms that can be viewed quantitatively and/or qualitatively. The meaning of the terms is frequently dependent on the context in which they are used. By way of example, two agents that both activate a receptor can be viewed as having a comparable effect from a qualitative perspective, but the two agents can be viewed as lacking a comparable effect from a quantitative perspective if one agent is only able to achieve 20% of the activity of the other agent as determined in an art-accepted assay (e.g., a dose-response assay) or in an art-accepted animal model. When comparing one result to another result (e.g., one result to a reference standard), "comparable" frequently (though not always) means that one result deviates from a reference standard by less than 35%, by less than 30%, by less than 25%, by less than 20%, by less than 15%, by less than 10%, by less than 7%, by less than 5%, by less than 4%, by less than 3%, by less than 2%, or by less than 1%. In particular embodiments, one result is comparable to a reference standard if it deviates by less than 15%, by less than 10%, or by less than 5% from the reference standard. By way of example, but not limitation, the activity or effect may refer to efficacy, stability, solubility, or immunogenicity.

"Substantially pure" indicates that a component makes up greater than about 50% of the total content of the composition, and typically greater than about 60% of the total polypeptide content. More typically, "substantially pure" refers to compositions in which at least 75%, at least 85%, at least 90% or more of the total composition is the component of interest. In some cases, the polypeptide will make up greater than about 90%, or greater than about 95% of the total content of the composition.

The terms "specifically binds" or "selectively binds", when referring to a ligand/receptor, antibody/antigen, or other binding pair, indicates a binding reaction which is determinative of the presence of the protein in a heterogeneous population of proteins and other biologics. Thus, under designated conditions, a specified ligand binds to a particular receptor and does not bind in a significant amount to other proteins present in the sample. The antibody, or binding composition derived from the antigen-binding site of an antibody, of the contemplated method binds to its antigen, or a variant or mutein thereof, with an affinity that is at least two-fold greater, at least ten times greater, at least 20-times greater, or at least 100-times greater than the affinity with any other antibody, or binding composition derived therefrom. In a particular embodiment, the antibody will have an affinity that is greater than about 109 liters/mol, as determined by, e.g., Scatchard analysis (Munsen, et al. 1980 Analyt. Biochem. 107:220-239).

The term "response," for example, of a cell, tissue, organ, or organism, encompasses a change in biochemical or physiological behavior, e.g., concentration, density, adhesion, or migration within a biological compartment, rate of gene expression, or state of differentiation, where the change is correlated with activation, stimulation, or treatment, or with internal mechanisms such as genetic programming. In certain contexts, the terms "activation", "stimulation", and the like refer to cell activation as regulated by internal mechanisms, as well as by external or environmental factors; whereas the terms "inhibition", "down-regulation" and the like refer to the opposite effects.

The terms "polypeptide," "peptide," and "protein", used interchangeably herein, refer to a polymeric form of amino acids of any length, which can include genetically coded and non-genetically coded amino acids, chemically or biochemically modified or derivatized amino acids, and polypeptides having modified polypeptide backbones. The terms include fusion proteins, including, but not limited to, fusion proteins with a heterologous amino acid sequence, fusion proteins with heterologous and homologous leader sequences, with or without N-terminus methionine residues; immunologically tagged proteins; and the like.

As used herein, the terms "variants" and "homologs" are used interchangeably to refer to amino acid or DNA sequences that are similar to reference amino acid or nucleic acid sequences, respectively. The term encompasses naturally-occurring variants and non-naturally-occurring variants. Naturally-occurring variants include homologs (polypeptides and nucleic acids that differ in amino acid or nucleotide sequence, respectively, from one species to another), and allelic variants (polypeptides and nucleic acids that differ in amino acid or nucleotide sequence, respectively, from one individual to another within a species). Thus, variants and homologs encompass naturally occurring DNA sequences and proteins encoded thereby and their isoforms, as well as splice variants of a protein or gene. The terms also encompass nucleic acid sequences that vary in one or more bases from a naturally-occurring DNA sequence but still translate into an amino acid sequence that corresponds to the naturally-occurring protein due to degeneracy of the genetic code. Non-naturally-occurring variants and homologs include polypeptides and nucleic acids that comprise a change in amino acid or nucleotide sequence, respectively, where the change in sequence is artificially introduced (e.g., muteins); for example, the change is generated in the laboratory by human intervention ("hand of man"). Therefore, non-naturally occurring variants and homologs may also refer to those that differ from the naturally-occurring sequences by one or more conservative substitutions and/or tags and/or conjugates.

The term "muteins" as used herein refers broadly to mutated recombinant proteins. These proteins usually carry single or multiple amino acid substitutions and are frequently derived from cloned genes that have been subjected to site-directed or random mutagenesis, or from completely synthetic genes.

The terms "DNA", "nucleic acid", "nucleic acid molecule", "polynucleotide" and the like are used interchangeably herein to refer to a polymeric form of nucleotides of any length, either deoxyribonucleotides or ribonucleotides, or analogs thereof. Non-limiting examples of polynucleotides include linear and circular nucleic acids, messenger RNA (mRNA), complementary DNA (cDNA), recombinant polynucleotides, vectors, probes, primers and the like.

Adenosine $A_{2A}$ Receptor and adenosine $A_{2B}$ Receptor and Inhibition Thereof A precise understanding of Compound I's underlying mechanism of action by which the compound effects its activity is not required to practice the invention. Compound I is believed to inhibit adenosine $A_{2A}$ receptor ($A_{2A}R$) and the adenosine $A_{2B}$ receptor ($A_{2B}R$). Alternatively, Compound I may inhibit adenylyl cyclase function. The compounds (or a subset thereof) may also have inhibitor activity on the $A_{2A}$ receptor ($A_{2A}R$), the adenosine $A_{2B}$ receptor ($A_{2B}R$) as well as adenylyl cyclase. Although the compounds of the invention are generally referred to herein as adenosine $A_{2A}$ receptor ($A_{2A}R$) and/or the adenosine $A_{2B}$ receptor ($A_{2B}R$) inhibitors, it is to be understood that the term "$A_{2A}R/A_{2B}R$ inhibitors" encompasses compounds that act individually through inhibition of $A_{2A}R$, $A_{2B}R$ or adenylyl cyclase, and/or compounds that act through inhibition of $A_{2A}R$, $A_{2B}R$, and adenylyl cyclase.

Methods of Treatment

In one aspect, provided herein is a method of treating a disease, disorder, or condition, mediated at least in part by the adenosine $A_{2A}$ receptor ($A_{2A}R$) or the adenosine $A_{2B}$ receptor ($A_{2B}R$), said method comprising administering to a subject in need thereof a total daily dosage of about 5 to 250 mg of Compound I, having the formula

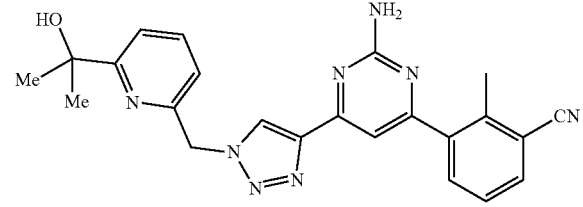
(Compound I)

or a pharmaceutically acceptable salt thereof.

In some embodiments, the therapeutically effective amount of Compound I is a total daily dosage of about 5 mg to 250 mg (e.g., about 5, 10, 15, 20, 25, 30, 35, 40, 45, 50, 55, 60, 65, 70, 75, 80, 85, 90, 95, 100, 110, 120, 130, 140, 150, 160, 170, 180, 190, 200, 210, 220, 230, 240, or 250 mg/day).

In some embodiments, the total daily dosage of Compound I is from about 120 to 180 mg per day. In some embodiments, the total daily dosage of Compound I is from about 130 to 170 mg per day. In some embodiments, the total daily dosage of Compound I is from about 140 to 160 mg per day. In some embodiments, the total daily dosage of Compound I is about 150 mg per day.

In some embodiments, the total daily dosage of Compound I is from about 95 to 155 mg per day. In some embodiments, the total daily dosage of Compound I is from about 105 to 145 mg per day. In some embodiments, the total daily dosage of Compound I is from about 115 to 135 mg per day. In some embodiments, the total daily dosage of Compound I is about 125 mg per day.

In some embodiments, the total daily dosage of Compound I is from about 50 to 150 mg per day. In some embodiments, the total daily dosage of Compound I is from about 70 to 130 mg per day. In some embodiments, the total daily dosage of Compound I is from about 90 to 110 mg per day. In some embodiments, the total daily dosage of Compound I is about 100 mg per day.

In some embodiments, the total daily dosage of Compound I is from about 45 to 105 mg per day. In some embodiments, the total daily dosage of Compound I is from about 55 to 95 mg per day. In some embodiments, the total daily dosage of Compound I is from about 65 to 85 mg per day. In some embodiments, the total daily dosage of Compound I is about 75 mg per day.

In some embodiments, the total daily dosage of Compound I is from about 10 to 40 mg per day. In some embodiments, the total daily dosage of Compound I is from about 15 to 35 mg per day. In some embodiments, the total daily dosage of Compound I is from about 20 to 30 mg per day. In some embodiments, the total daily dosage of Compound I is about 25 mg per day.

In some embodiments, the total daily dosage of Compound I is from about 5 to 15 mg per day. In some embodiments, the total daily dosage of Compound I is from about 7.5 to 12.5 mg per day. In some embodiments, the total daily dosage of Compound I is about 10 mg per day.

In some embodiments, the total daily dosage of Compound I is from about 10 to 25 mg per day. In some embodiments, the total daily dosage of Compound I is from about 75 to 150 mg per day. In some embodiments, the total daily dosage of Compound I is from about 125 to 150 mg per day.

In some embodiments, Compound I is administered orally. In some embodiments, Compound I is administered daily in single, divided, or continuous doses. In some embodiments, Compound I is administered twice daily. Further administration routes, dosages, and timing are discussed in the following sections.

In some embodiments, the subject receives daily dosages of Compound I for a period of from 1 to 36 months. In some embodiments, said subject receives daily dosages of Compound I for at least 3 months. In some embodiments, said subject receives daily dosages of Compound I for at least 6 months. In some embodiments, said subject receives daily dosages of Compound I for at least 9 months. In some embodiments, said subject receives daily dosages of Compound I for at least 12 months. In some embodiments, said subject receives daily dosages of Compound I for at least 15 months. In some embodiments, said subject receives daily dosages of Compound I for at least 18 months. In some embodiments, said subject receives daily dosages of Compound I for at least 21 months. In some embodiments, said subject receives daily dosages of Compound I for at least 24 months. In some embodiments, said subject receives daily dosages of Compound I for at least 30 months. In some embodiments, said subject receives daily dosages of Compound I for at least 33 months. In some embodiments, said subject receives daily dosages of Compound I for at least 36 months.

Therapeutic and Prophylactic Uses

The methods described herein are useful in the treatment or prevention of a broad range of diseases, disorders and/or conditions, and/or the symptoms thereof. While particular uses are described in detail hereafter, it is to be understood that the present disclosure is not so limited. Furthermore, although general categories of particular diseases, disorders and conditions are set forth hereafter, some of the diseases, disorders and conditions may be a member of more than one category, and others may not be a member of any of the disclosed categories.

In some embodiments, the diseases, disorders and/or conditions described herein are mediated, at least in part, by the adenosine $A_{2A}$ receptor ($A_{2A}R$). In some embodiments, the diseases, disorders and/or conditions described herein are mediated, at least in part, by the adenosine $A_{2B}$ receptor ($A_{2B}R$). In some embodiments, the diseases, disorders and/or conditions described herein are mediated, at least in part, by both $A_{2A}R$ and $A_{2B}R$.

In some embodiments, Compound I is administered in an amount effective to reverse or stop the progression of $A_{2A}R$-mediated immunosuppression Oncology-Related Disorders.

In accordance with the present disclosure, Compound I can be used to treat or prevent a proliferative condition or disorder, including a cancer, for example, cancer of the uterus, cervix, breast, prostate, testes, gastrointestinal tract (e.g., esophagus, oropharynx, stomach, small or large intestines, colon, or rectum), kidney, renal cell, bladder, bone, bone marrow, skin, head or neck, liver, gall bladder, heart, lung, pancreas, salivary gland, adrenal gland, thyroid, brain (e.g., gliomas), ganglia, central nervous system (CNS) and peripheral nervous system (PNS), and cancers of the hematopoietic system and the immune system (e.g., spleen or thymus). The present disclosure also provides methods of treating or preventing other cancer-related diseases, disorders or conditions, including, for example, immunogenic tumors, non-immunogenic tumors, dormant tumors, virus-induced cancers (e.g., epithelial cell cancers, endothelial cell cancers, squamous cell carcinomas and papillomavirus), adenocarcinomas, lymphomas, carcinomas, melanomas, leukemias, myelomas, sarcomas, teratocarcinomas, chemically-induced cancers, metastasis, and angiogenesis. The invention contemplates reducing tolerance to a tumor cell or cancer cell antigen, e.g., by modulating activity of a regulatory T-cell and/or a CD8+ T-cell (see, e.g., Ramirez-Montagut, et al. (2003) *Oncogene* 22:3180-87; and Sawaya, et al. (2003) *New Engl. J. Med.* 349:1501-09). In particular embodiments, the tumor or cancer is colon cancer, ovarian cancer, breast cancer, melanoma, lung cancer, glioblastoma, or leukemia. The use of the term(s) cancer-related diseases, disorders and conditions is meant to refer broadly to conditions that are associated, directly or indirectly, with cancer, and includes, e.g., angiogenesis and precancerous conditions such as dysplasia.

In some embodiments, the cancer is melanoma, colon cancer, pancreatic cancer, breast cancer, prostate cancer, lung cancer, leukemia, a brain tumor, lymphoma, ovarian cancer, or Kaposi's sarcoma.

In some embodiments, the cancer is non-small-cell lung carcinoma, colorectal cancer, head and neck squamous cell carcinoma, ovarian cancer, triple-negative breast cancer, renal cell carcinoma, prostate cancer, esophageal cancer, or gastroesophageal cancer. In some embodiments, the cancer is non-small-cell lung carcinoma. In some embodiments, the cancer is colorectal cancer. In some embodiments, the cancer is head and neck squamous cell carcinoma. In some embodiments, the cancer is ovarian cancer. In some embodiments, the cancer is triple-negative breast cancer. In some embodiments, the cancer is renal cell carcinoma. In some embodiments, the cancer is prostate cancer. In some embodiments, the cancer is esophageal cancer. In some embodiments, the cancer is gastroesophageal cancer.

In certain embodiments, a cancer can be metastatic or at risk of becoming metastatic, or may occur in a diffuse tissue, including cancers of the blood or bone marrow (e.g., leukemia). In some further embodiments, the compounds of the invention can be used to overcome T-cell tolerance.

In some embodiments, the present invention provides methods for treating a proliferative condition, cancer, tumor, or precancerous condition with Compound I and at least one additional therapeutic or diagnostic agent, examples of which are set forth elsewhere herein.

Immune- and Inflammatory-Related Disorders.

As used herein, terms such as "immune disease", "immune condition", "immune disorder", "inflammatory disease", "inflammatory condition", "inflammatory disorder" and the like are meant to broadly encompass any immune-related condition (e.g., an autoimmune disease) or a disorder with an inflammatory component that can be treated by Compound I such that some therapeutic benefit is obtained. Such conditions frequently are inextricably intertwined with other diseases, disorders and conditions. By way of example, an "immune condition" may refer to proliferative conditions, such as cancer, tumors, and angiogenesis; including infections (acute and chronic), tumors, and cancers that resist eradication by the immune system.

Compound I can be used to increase or enhance an immune response; to improve immunization, including increasing vaccine efficacy; and to increase inflammation. Immune deficiencies associated with immune deficiency diseases, immunosuppressive medical treatment, acute and/or chronic infection, and aging can be treated using the compounds disclosed herein. Compound I can also be used to stimulate the immune system of patients suffering from iatrogenically-induced immune suppression, including those who have undergone bone marrow transplants, chemotherapy, or radiotherapy.

In particular embodiments of the present disclosure, Compound I is used to increase or enhance an immune response to an antigen by providing adjuvant activity. In a particular embodiment, at least one antigen or vaccine is administered to a subject in combination with Compound I to prolong an immune response to the antigen or vaccine. Therapeutic compositions are also provided which include at least one antigenic agent or vaccine component, including, but not limited to, viruses, bacteria, and fungi, or portions thereof, proteins, peptides, tumor-specific antigens, and nucleic acid vaccines, in combination with Compound I.

A non-limiting list of immune- and inflammatory-related diseases, disorders and conditions which may be treated or prevented with the compounds and compositions of the present invention include, arthritis (e.g., rheumatoid arthritis), kidney failure, lupus, asthma, psoriasis, colitis, pancreatitis, allergies, fibrosis, surgical complications (e.g., where inflammatory cytokines prevent healing), anemia, and fibromyalgia. Other diseases and disorders which may be associated with chronic inflammation include Alzheimer's disease, congestive heart failure, stroke, aortic valve stenosis, arteriosclerosis, osteoporosis, Parkinson's disease, infections, inflammatory bowel disease (e.g., Crohn's disease and ulcerative colitis), allergic contact dermatitis and other eczemas, systemic sclerosis, transplantation and multiple sclerosis.

Among other immune-related disorders, it is contemplated that inhibition of $A_{2A}R/A_{2B}R$ function may also play a role in immunologic tolerance and prevention of fetal rejection in utero.

In some embodiments, Compound I can be combined with an immunosuppressive agent to reduce the number of immune effector cells.

Some of the aforementioned diseases, disorders and conditions for which Compound I is particularly efficacious (due to, for example, limitations of current therapies) are described in more detail hereafter.

Rheumatoid Arthritis (RA), which is generally characterized by chronic inflammation in the membrane lining (the synovium) of the joints, affects approximately 1% of the U.S. population (—2.1 million people). Further understanding of the role of cytokines, including TNF-α and IL-1, in the inflammatory process has enabled the development and introduction of a new class of disease-modifying antirheumatic drugs (DMARDs). Agents (some of which overlap with treatment modalities for RA) include ENBREL (etanercept), REMICADE (infliximab), HUMIRA (adalimumab) and KINERET (anakinra) Though some of these agents relieve symptoms, inhibit progression of structural damage, and improve physical function in particular patient populations, there is still a need for alternative agents with improved efficacy, complementary mechanisms of action, and fewer/less severe adverse effects.

Psoriasis, a constellation of common immune-mediated chronic skin diseases, affects more than 4.5 million people in the U.S., of which 1.5 million are considered to have a moderate-to severe form of the disease. Moreover, over 10% of patients with psoriasis develop psoriatic arthritis, which damages the bone and connective tissue around the joints. An improved understanding of the underlying physiology of psoriasis has resulted in the introduction of agents that, for example, target the activity of T lymphocytes and cytokines responsible for the inflammatory nature of the disease. Such agents include the TNF-α inhibitors (also used in the treatment of rheumatoid arthritis (RA)), including ENBREL (etanercept), REMICADE (infliximab) and HUMIRA (adalimumab)), and T-cell inhibitors such as AMEVIVE (alefacept) and RAPTIVA (efalizumab). Though several of these agents are effective to some extent in certain patient populations, none have been shown to effectively treat all patients.

Microbial-Related Disorders.

The present invention contemplates the use of Compound I in the treatment and/or prevention of any viral, bacterial, fungal, parasitic or other infective disease, disorder or condition for which treatment with Compound I may be beneficial.

Examples of viral diseases, disorders and conditions that are contemplated include, but are not limited to, hepatitis B virus (HBV), hepatitis C virus (HCV), human papilloma virus (HPV), HIV, AIDS (including its manifestations such as cachexia, dementia, and diarrhea), herpes simplex virus (HSV), Epstein-Barr virus (EBV), varicella zoster virus, coxsackie virus, and cytomegalovirus (CMV).

Further examples of such diseases and disorders include staphylococcal and streptococcal infections (e.g., *Staphylococcus aureus* and *streptococcus sanguinis*, respectively), *leishmania, toxoplasma, trichomonas,* giardia, *Candida albicans, Bacillus anthracis*, and *Pseudomonas aeruginosa*. In some embodiments, diseases or disorders include *Mycobacterium* infection (e.g., *Mycobacterium leprae* or *Mycobacterium tuberculosis*) or an infection caused by *Listeria monocytogenes* or Toxplasma *gondii*. Compounds of the invention can be used to treat sepsis, decrease or inhibit bacterial growth, and reduce or inhibit inflammatory cytokines.

Further embodiments contemplate the treatment of a parasitic infection including, but not limited to, *Leishmania donovani, Leishmania tropica, Leishmania major, Leishmania aethiopica, Leishmania mexicana, Plasmodium falciparum, Plasmodium vivax, Plasmodium ovale,* or *Plasmodium malariae*. Frequently, anti-parasitic therapy is administered prophylactically (e.g., before a subject travels to an area with a high frequency of parasitic infection).

CNS-Related and Neurological Disorders.

Inhibition of $A_{2A}R/A_{2B}R$ may also be an important treatment strategy for patients with neurological, neuropsychiatric, neurodegenerative or other diseases, disorders and conditions having some association with the central nervous system, including disorders associated with impairment of cognitive function and motor function. Examples include Parkinson's disease, extra pyramidal syndrome (EPS), dystonia, akathisia, tardive dyskinesia, restless leg syndrome (RLS), epilepsy, periodic limb movement in sleep (PLMS), attention deficit disorders, depression, anxiety, dementia, Alzheimer's disease, Huntington's disease, multiple sclerosis, cerebral ischemia, hemorrhagic stroke, subarachnoid hemorrhage, and traumatic brain injury.

Subjects suffering from multiple sclerosis (MS), a seriously debilitating autoimmune disease comprising multiple areas of inflammation and scarring of the myelin in the brain and spinal cord, may be particularly helped by Compound I, as current treatments only alleviate symptoms or delay the progression of disability.

Similarly, Compound I may be particularly advantageous for subjects afflicted with neurodegenerative disorders, such as Alzheimer's disease (AD), a brain disorder that seriously impairs patients' thought, memory, and language processes; and Parkinson's disease (PD), a progressive disorder of the CNS characterized by, for example, abnormal movement, rigidity and tremor. These disorders are progressive and debilitating, and no curative agents are available.

Other Disorders.

Embodiments of the present invention contemplate the administration of Compound I to a subject for the treatment or prevention of any other disorder that may benefit from at least some level of $A_{2A}R/A_{2B}R$ inhibition. Such diseases, disorders and conditions include, for example, cardiovascular (e.g., cardiac ischemia), gastrointestinal (e.g., Crohn's disease), metabolic (e.g., diabetes), hepatic (e.g., hepatic fibrosis, NASH, and NAFLD), pulmonary (e.g., COPD and asthma), ophthalmologic (e.g., diabetic retinopathy), and renal (e.g., renal failure) disorders.

Pharmaceutical Compositions

Compound I may be in the form of compositions suitable for administration to a subject. In general, such compositions are "pharmaceutical compositions" comprising Compound I and one or more pharmaceutically acceptable or physiologically acceptable diluents, carriers or excipients. The pharmaceutical compositions may be used in the methods of the present invention; thus, for example, the pharmaceutical compositions can be administered ex vivo or in vivo to a subject in order to practice the therapeutic and prophylactic methods and uses described herein.

The pharmaceutical compositions of the present invention can be formulated to be compatible with the intended method or route of administration; exemplary routes of administration are set forth herein. Furthermore, the pharmaceutical compositions may be used in combination with other therapeutically active agents or compounds as described herein in order to treat or prevent the diseases, disorders and conditions as contemplated by the present invention.

The pharmaceutical compositions containing Compound I may be in a form suitable for oral use, for example, as tablets, capsules, troches, lozenges, aqueous or oily suspensions, dispersible powders or granules, emulsions, hard or soft capsules, or syrups, solutions, microbeads or elixirs. Pharmaceutical compositions intended for oral use may be prepared according to any method known to the art for the manufacture of pharmaceutical compositions, and such compositions may contain one or more agents such as, for example, sweetening agents, flavoring agents, coloring agents and preserving agents in order to provide pharmaceutically elegant and palatable preparations. Tablets, capsules and the like contain the active ingredient in admixture with non-toxic pharmaceutically acceptable excipients which are suitable for the manufacture of tablets. These excipients may be, for example, diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc.

The tablets, capsules and the like suitable for oral administration may be uncoated or coated by known techniques to delay disintegration and absorption in the gastrointestinal tract and thereby provide a sustained action. For example, a time-delay material such as glyceryl monostearate or glyceryl distearate may be employed. They may also be coated by techniques known in the art to form osmotic therapeutic tablets for controlled release. Additional agents include biodegradable or biocompatible particles or a polymeric substance such as polyesters, polyamine acids, hydrogel, polyvinyl pyrrolidone, polyanhydrides, polyglycolic acid, ethylene-vinylacetate, methylcellulose, carboxymethylcellulose, protamine sulfate, or lactide/glycolide copolymers, polylactide/glycolide copolymers, or ethylenevinylacetate copolymers in order to control delivery of an administered composition. For example, the oral agent can be entrapped in microcapsules prepared by coacervation techniques or by interfacial polymerization, by the use of hydroxymethylcellulose or gelatin-microcapsules or poly (methylmethacrolate) microcapsules, respectively, or in a colloid drug delivery system. Colloidal dispersion systems include macromolecule complexes, nano-capsules, microspheres, microbeads, and lipid-based systems, including oil-in-water emulsions, micelles, mixed micelles, and liposomes. Methods for the preparation of the above-mentioned formulations will be apparent to those skilled in the art.

Formulations for oral use may also be presented as hard gelatin capsules wherein the active ingredient is mixed with an inert solid diluent, for example, calcium carbonate, calcium phosphate, kaolin or microcrystalline cellulose, or as soft gelatin capsules wherein the active ingredient is mixed with water or an oil medium, for example peanut oil, liquid paraffin, or olive oil.

The pharmaceutical compositions typically comprise 5 to 250 mg of Compound I contemplated by the present invention and one or more pharmaceutically and physiologically acceptable formulation agents.

In some embodiments, pharmaceutical compositions comprise from about 120 to 180 mg of Compound I. In some embodiments, pharmaceutical compositions comprise from about 130 to 170 mg of Compound I. In some embodiments, pharmaceutical compositions comprise from about 140 to 160 mg of Compound I. In some embodiments, pharmaceutical compositions comprise about 150 mg of Compound I.

In some embodiments, pharmaceutical compositions comprise from about 95 to 155 mg of Compound I. In some embodiments, pharmaceutical compositions comprise from about 105 to 145 mg of Compound I. In some embodiments, pharmaceutical compositions comprise from about 115 to 135 mg of Compound I. In some embodiments, pharmaceutical compositions comprise about 125 mg of Compound I.

In some embodiments, pharmaceutical compositions comprise from about 50 to 150 mg of Compound I. In some embodiments, pharmaceutical compositions comprise from about 70 to 130 mg of Compound I. In some embodiments, pharmaceutical compositions comprise from about 90 to 110 mg of Compound I. In some embodiments, pharmaceutical compositions comprise about 100 mg of Compound I.

In some embodiments, pharmaceutical compositions comprise from about 45 to 105 mg of Compound I. In some embodiments, pharmaceutical compositions comprise from about 55 to 95 mg of Compound I. In some embodiments, pharmaceutical compositions comprise from about 65 to 85 mg of Compound I. In some embodiments, pharmaceutical compositions comprise about 75 mg of Compound I.

In some embodiments, pharmaceutical compositions comprise from about 25 to 75 mg of Compound I. In some embodiments, pharmaceutical compositions comprise from about 35 to 65 mg of Compound I. In some embodiments, pharmaceutical compositions comprise from about 45 to 55 mg of Compound I. In some embodiments, pharmaceutical compositions comprise about 50 mg of Compound I.

In some embodiments, pharmaceutical compositions comprise from about 10 to 40 mg of Compound I. In some embodiments, pharmaceutical compositions comprise from about 15 to 35 mg of Compound I. In some embodiments, pharmaceutical compositions comprise from about 20 to 30 mg of Compound I. In some embodiments, pharmaceutical compositions comprise about 25 mg of Compound I.

In some embodiments, pharmaceutical compositions comprise from about 5 to 15 mg of Compound I. In some embodiments, pharmaceutical compositions comprise from about 7.5 to 12.5 mg of Compound I. In some embodiments, pharmaceutical compositions comprise about 10 mg of Compound I.

In some embodiments, pharmaceutical compositions comprise from about 25 to 50 mg of Compound I. In some embodiments, pharmaceutical compositions comprise from about 75 to 100 mg of Compound I. In some embodiments, pharmaceutical compositions comprise from about 125 to 150 mg of Compound I.

Suitable pharmaceutically acceptable or physiologically acceptable diluents, carriers or excipients include, but are not limited to, antioxidants (e.g., ascorbic acid and sodium bisulfate), preservatives (e.g., benzyl alcohol, methyl parabens, ethyl or n-propyl, p-hydroxybenzoate), emulsifying agents, suspending agents, dispersing agents, solvents, fillers, bulking agents, detergents, buffers, vehicles, diluents, and/or adjuvants. For example, a suitable vehicle may be physiological saline solution or citrate buffered saline, possibly supplemented with other materials common in pharmaceutical compositions for parenteral administration. Neutral buffered saline or saline mixed with serum albumin are further exemplary vehicles. Those skilled in the art will readily recognize a variety of buffers that can be used in the pharmaceutical compositions and dosage forms contemplated herein. Typical buffers include, but are not limited to, pharmaceutically acceptable weak acids, weak bases, or mixtures thereof. As an example, the buffer components can be water soluble materials such as phosphoric acid, tartaric acids, lactic acid, succinic acid, citric acid, acetic acid, ascorbic acid, aspartic acid, glutamic acid, and salts thereof. Acceptable buffering agents include, for example, a Tris buffer, N-(2-Hydroxyethyl)piperazine-N'-(2-ethanesulfonic acid) (HEPES), 2-(N-Morpholino)ethanesulfonic acid (MES), 2-(N-Morpholino)ethanesulfonic acid sodium salt (MES), 3-(N-Morpholino)propanesulfonic acid (MOPS), and N-tris[Hydroxymethyl]methyl-3-aminopropanesulfonic acid (TAPS).

Pharmaceutical Dosage Forms

The present disclosure also includes pharmaceutical dosage forms of Compound I, or a pharmaceutically acceptable salt thereof. The dosage forms described herein are suitable for oral administration to a subject.

In some embodiments, the present disclosure provides a single unit dosage capsule or tablet form containing 5-250 mg of Compound I, having the formula:

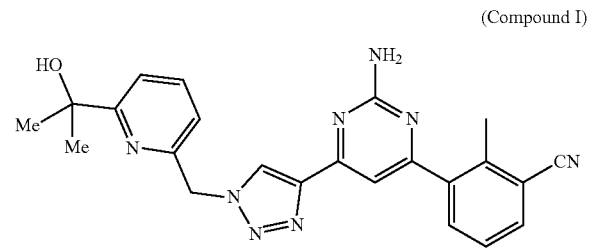 [SMILES: Cc1c(C#N)cccc1-c1cc(-c2cn(Cc3cccc(C(C)(C)O)n3)nn2)nc(N)n1]

(Compound I)

or a pharmaceutically acceptable salt thereof.

In some embodiments, the single unit dosage is a capsule.

In some embodiments, the single unit dosage is a tablet.

In some embodiments, the single unit dosage capsule or tablet comprises about 10, 25, 50, 75, 100, 150, 200, or 250 mg of Compound I.

In some embodiments, the single unit dosage capsule comprises from about 120 to 180 mg of Compound I. In some embodiments, the single unit dosage capsule comprises from about 130 to 170 mg of Compound I. In some embodiments, the single unit dosage capsule comprises from about 140 to 160 mg of Compound I. In some embodiments, the single unit dosage capsule comprises about 150 mg of Compound I.

In some embodiments, the single unit dosage capsule comprises from about 95 to 155 mg of Compound I. In some embodiments, the single unit dosage capsule comprises from about 105 to 145 mg of Compound I. In some embodiments, the single unit dosage capsule comprises from about 115 to 135 mg of Compound I. In some embodiments, the single unit dosage capsule comprises about 125 mg of Compound I.

In some embodiments, the single unit dosage capsule or tablet comprises from about 50 to 150 mg of Compound I. In some embodiments, the single unit dosage capsule or tablet comprises from about 70 to 130 mg of Compound I. In some embodiments, the single unit dosage capsule or tablet comprises from about 90 to 110 mg of Compound I. In some embodiments, the single unit dosage capsule or tablet comprises about 100 mg of Compound I.

In some embodiments, the single unit dosage capsule or tablet comprises from about 45 to 105 mg of Compound I. In some embodiments, the single unit dosage capsule or tablet comprises from about 55 to 95 mg of Compound I. In some embodiments, the single unit dosage capsule or tablet comprises from about 65 to 85 mg of Compound I. In some embodiments, the single unit dosage capsule or tablet comprises about 75 mg of Compound I.

In some embodiments, the single unit dosage capsule or tablet comprises from about 25 to 75 mg of Compound I. In some embodiments, the single unit dosage capsule or tablet comprises from about 35 to 65 mg of Compound I. In some embodiments, the single unit dosage capsule or tablet comprises from about 45 to 55 mg of Compound I. In some embodiments, the single unit dosage capsule or tablet comprises about 50 mg of Compound I.

In some embodiments, the single unit dosage capsule or tablet comprises from about 10 to 40 mg of Compound I. In some embodiments, the single unit dosage capsule or tablet comprises from about 15 to 35 mg of Compound I. In some embodiments, the single unit dosage capsule or tablet comprises from about 20 to 30 mg of Compound I. In some embodiments, the single unit dosage capsule or tablet comprises about 25 mg of Compound I.

In some embodiments, the single unit dosage capsule or tablet comprises from about 5 to 15 mg of Compound I. In some embodiments, the single unit dosage capsule or tablet comprises from about 7.5 to 12.5 mg of Compound I. In some embodiments, the single unit dosage capsule or tablet comprises about 10 mg of Compound I.

In some embodiments, the single unit dosage capsule or tablet comprises from about 10 to 25 mg of Compound I. In some embodiments, the single unit dosage capsule or tablet comprises from about 75 to 150 mg of Compound I. In some embodiments, the single unit dosage capsule or tablet comprises from about 125 to 150 mg of Compound I.

In some embodiments, the single unit dosage form is a capsule and is in a capsule of size #000, #00E, #00, #0E, #0, #1, #2, #3, #4, or #5. In some embodiments, the single unit dosage form is in a capsule of size #4. In some embodiments, the single unit dosage form is in a capsule of size #5.

Routes of Administration

The present invention contemplates the administration of Compound I, and compositions thereof, in any appropriate manner. Suitable routes of administration include oral, parenteral (e.g., intramuscular, intravenous, subcutaneous (e.g., injection or implant), intraperitoneal, intracisternal, intraarticular, intraperitoneal, intracerebral (intraparenchymal) and intracerebroventricular), nasal, vaginal, sublingual, intraocular, rectal, topical (e.g., transdermal), buccal and inhalation. Depot injections, which are generally administered subcutaneously or intramuscularly, may also be utilized to release the Compound I over a defined period of time.

In some embodiments, Compound I is administered orally. In some embodiments, Compound I is administered once daily. In some embodiments, Compound I is administered twice daily.

Combination Therapy

The present invention contemplates the use of Compound I in combination with one or more active therapeutic agents (e.g., chemotherapeutic agents) or other prophylactic or therapeutic modalities (e.g., radiation). In such combination therapy, the various active agents frequently have different, complementary mechanisms of action. Such combination therapy may be especially advantageous by allowing a dose reduction of one or more of the agents, thereby reducing or eliminating the adverse effects associated with one or more of the agents. Furthermore, such combination therapy may have a synergistic therapeutic or prophylactic effect on the underlying disease, disorder, or condition.

As used herein, "combination" is meant to include therapies that can be administered separately, for example, formulated separately for separate administration (e.g., as may be provided in a kit), and therapies that can be administered together in a single formulation (i.e., a "co-formulation").

In certain embodiments, the Compound I administered or applied sequentially, e.g., where one agent is administered prior to one or more other agents. In other embodiments, the Compound I is administered simultaneously, e.g., where two or more agents are administered at or about the same time; the two or more agents may be present in two or more separate formulations or combined into a single formulation (i.e., a co-formulation). Regardless of whether the two or more agents are administered sequentially or simultaneously, they are considered to be administered in combination for purposes of the present invention.

Compound I may be used in combination with at least one other (active) agent in any manner appropriate under the circumstances. In one embodiment, treatment with the at least one active agent and Compound I is maintained over a period of time. In another embodiment, treatment with the at least one active agent is reduced or discontinued (e.g., when the subject is stable), while treatment with Compound I of the present invention is maintained at a constant dosing regimen. In a further embodiment, treatment with the at least one active agent is reduced or discontinued (e.g., when the subject is stable), while treatment with Compound I is reduced (e.g., lower dose, less frequent dosing or shorter treatment regimen). In yet another embodiment, treatment with the at least one active agent is reduced or discontinued (e.g., when the subject is stable), and treatment with Compound I is increased (e.g., higher dose, more frequent dosing or longer treatment regimen). In yet another embodiment, treatment with the at least one active agent is maintained and treatment with Compound I is reduced or discontinued (e.g., lower dose, less frequent dosing or shorter treatment regimen). In yet another embodiment, treatment with the at least one active agent and treatment with Compound I is reduced or discontinued (e.g., lower dose, less frequent dosing or shorter treatment regimen).

Oncology-Related Disorders.

The present invention provides methods for treating and/or preventing a proliferative condition, cancer, tumor, or precancerous disease, disorder or condition with Compound I and at least one additional therapeutic or diagnostic agent. In some embodiments, the additional therapeutic or diagnostic agent is radiation, an immunomodulatory agent or chemotherapeutic agent, or diagnostic agent. Suitable immunomodulatory agents that may be used in the present invention include CD4OL, B7, and B7RP1; activating monoclonal antibodies (mAbs) to stimulatory receptors, such as, anti-CD40, anti-CD38, anti-ICOS, and 4-IBB ligand; dendritic cell antigen loading (in vitro or in vivo); anti-cancer vaccines such as dendritic cell cancer vaccines; cytokines/chemokines, such as, ILL IL2, IL12, IL18, ELC/CCL19, SLC/CCL21, MCP-1, IL-4, IL-18, TNF, IL-15, MDC, IFNa/b, M-CSF, IL-3, GM-CSF, IL-13, and anti-IL-10; bacterial lipopolysaccharides (LPS); and immune-stimulatory oligonucleotides.

In certain embodiments, the present invention provides methods for tumor suppression of tumor growth comprising administration of Compound I in combination with a signal transduction inhibitor (STI) to achieve additive or synergistic suppression of tumor growth. As used herein, the term "signal transduction inhibitor" refers to an agent that selectively inhibits one or more steps in a signaling pathway. Signal transduction inhibitors (STIs) of the present invention include: (i) bcr/abl kinase inhibitors (e.g., GLEEVEC); (ii) epidermal growth factor (EGF) receptor inhibitors, including kinase inhibitors and antibodies; (iii) her-2/neu receptor inhibitors (e.g., HERCEPTIN); (iv) inhibitors of Akt family kinases or the Akt pathway (e.g., rapamycin); (v) cell cycle kinase inhibitors (e.g., flavopiridol); (vi) phosphatidyl inositol kinase inhibitors; (vi) ALK inhibitors (e.g., crizotinib, ceritinib, alectinib), and (vii) BTK inhibitors (e.g., Ibrutinib, Acalabrutinib, GS-4059, BGB-3111, and HM71224. In some embodiments, compound administered with Compound I targets multiple protein tyrosine kinases (e.g. sorafenib, sunitinib, etc.) Agents involved in in immunomodulation can also be used in combination with Compound I for the suppression of tumor growth in cancer patients.

Examples of chemotherapeutic agents include, but are not limited to, alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamime; nitrogen mustards such as chiorambucil, chlomaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, caminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside (Ara-C); cyclophosphamide; thiotepa; taxoids, e.g., paclitaxel and doxetaxel; chlorambucil; gemcitabine; 6-thioguanine; mercaptopurine; methotrexate; platinum and platinum coordination complexes such as cisplatin, oxaliplatin and carboplatin; vinblastine; etoposide (VP-16); ifosfamide; mitomycin C; mitoxantrone; vincristine; vinorelbine; navelbine; novantrone; teniposide; daunomycin; aminopterin; xeloda; ibandronate; CPT11; topoisomerase inhibitors; difluoromethylomithine (DMFO); retinoic acid; esperamicins; capecitabine; and pharmaceutically acceptable salts, acids or derivatives of any of the above.

Chemotherapeutic agents also include anti-hormonal agents that act to regulate or inhibit hormonal action on tumors such as anti-estrogens, including for example tamoxifen, raloxifene, aromatase inhibiting 4(5)-imidazoles, 4-hydroxytamoxifen, trioxifene, keoxifene, onapristone, and toremifene; and antiandrogens such as flutamide, nilutamide, bicalutamide, leuprolide, and goserelin; and pharmaceutically acceptable salts, acids or derivatives of any of the above. In certain embodiments, combination therapy comprises administration of a hormone or related hormonal agent.

Additional treatment modalities that may be used in combination with Compound I include radiotherapy, a monoclonal antibody against a tumor antigen, a complex of a monoclonal antibody and toxin, a T-cell adjuvant, bone marrow transplant, or antigen presenting cells (e.g., dendritic cell therapy).

Immune Checkpoint Inhibitors. The present invention contemplates the use of the inhibitors of $A_{2A}R/A_{2B}R$ function described herein in combination with immune checkpoint inhibitors.

The tremendous number of genetic and epigenetic alterations that are characteristic of all cancers provides a diverse set of antigens that the immune system can use to distinguish tumor cells from their normal counterparts. In the case of T cells, the ultimate amplitude (e.g., levels of cytokine production or proliferation) and quality (e.g., the type of immune response generated, such as the pattern of cytokine production) of the response, which is initiated through antigen recognition by the T-cell receptor (TCR), is regulated by a balance between co-stimulatory and inhibitory signals (immune checkpoints). Under normal physiological conditions, immune checkpoints are crucial for the prevention of autoimmunity (i.e., the maintenance of self-tolerance) and also for the protection of tissues from damage when the immune system is responding to pathogenic infection. The expression of immune checkpoint proteins can be dysregulated by tumors as an important immune resistance mechanism.

T-cells have been the major focus of efforts to therapeutically manipulate endogenous antitumor immunity because of i) their capacity for the selective recognition of peptides derived from proteins in all cellular compartments; ii) their capacity to directly recognize and kill antigen-expressing cells (by CD8+ effector T cells; also known as cytotoxic T lymphocytes (CTLs)); and iii) their ability to orchestrate diverse immune responses by CD4+ helper T cells, which integrate adaptive and innate effector mechanisms.

In the clinical setting, the blockade of immune checkpoints—which results in the amplification of antigen-specific T cell responses—has shown to be a promising approach in human cancer therapeutics.

T cell-mediated immunity includes multiple sequential steps, each of which is regulated by counterbalancing stimulatory and inhibitory signals in order to optimize the response. While nearly all inhibitory signals in the immune response ultimately modulate intracellular signaling pathways, many are initiated through membrane receptors, the ligands of which are either membrane-bound or soluble (cytokines). While co-stimulatory and inhibitory receptors and ligands that regulate T-cell activation are frequently not overexpressed in cancers relative to normal tissues, inhibitory ligands and receptors that regulate T cell effector functions in tissues are commonly overexpressed on tumor cells or on non-transformed cells associated with the tumor microenvironment. The functions of the soluble and membrane-bound receptor—ligand immune checkpoints can be modulated using agonist antibodies (for co-stimulatory pathways) or antagonist antibodies (for inhibitory pathways). Thus, in contrast to most antibodies currently approved for cancer therapy, antibodies that block immune checkpoints do not target tumor cells directly, but rather target lymphocyte receptors or their ligands in order to enhance endogenous antitumor activity. [See Pardoll, (April 2012) Nature Rev. Cancer 12:252-64].

Examples of immune checkpoints (ligands and receptors), some of which are selectively upregulated in various types of tumor cells, that are candidates for blockade include PD1 (programmed cell death protein 1); PDL1 (PD1 ligand); BTLA (B and T lymphocyte attenuator); CTLA4 (cytotoxic T-lymphocyte associated antigen 4); TIM3 (T-cell membrane protein 3); LAG3 (lymphocyte activation gene 3); and Killer Inhibitory Receptors, which can be divided into two classes based on their structural features: i) killer cell immunoglobulin-like receptors (KIRs), and ii) C-type lectin receptors (members of the type II transmembrane receptor family). Other less well-defined immune checkpoints have been described in the literature, including both receptors (e.g., the 2B4 (also known as CD244) receptor) and ligands (e.g., certain B7 family inhibitory ligands such B7-H3 (also known as CD276) and B7-H4 (also known as B7-S1, B7x and VCTN1)). [See Pardoll, (April 2012) Nature Rev. Cancer 12:252-64]. Additional immune checkpoints that are candidate for blockage include Interleukin-2 receptor subunit beta (IL2RB (also known as CD122)) and its ligand IL-2. For example, NKTR-214 (a pegylated analogue of IL-2) is an agonist of CD122 and stimulates an individual's immune system (particular tumoricidal T cells and NK cells) to fight proliferative diseases.

The present invention contemplates the use of the inhibitors of $A_{2A}R/A_{2B}R$ function described herein in combination with inhibitors of the aforementioned immune-checkpoint receptors and ligands, as well as yet-to-be-described immune-checkpoint receptors and ligands. Certain modulators of immune checkpoints are currently available, whereas others are in late-stage development. To illustrate, when it was approved for the treatment of melanoma in 2011, the fully humanized CTLA4 monoclonal antibody ipilimumab (YERVOY; Bristol-Myers Squibb) became the first immune checkpoint inhibitor to receive regulatory approval in the US. Fusion proteins comprising CTLA4 and an antibody (CTLA4-Ig; abatcept (ORENCIA; Bristol-Myers Squibb)) have been used for the treatment of rheumatoid arthritis, and other fusion proteins have been shown to be effective in renal transplantation patients that are sensitized to Epstein Barr Virus. PD1 antibodies are under development (e.g., nivolumab (Bristol-Myers Squibb) and lambrolizumab (Merck)), and anti-PDL1 antibodies are also being evaluated (e.g., MPDL3280A (Roche)). Nivolumab has shown promise in patients with melanoma, lung and kidney cancer.

In one aspect of the present invention, Compound I is combined with an immuno-oncology agent that is (i) an agonist of a stimulatory (including a co-stimulatory) receptor or (ii) an antagonist of an inhibitory (including a co-inhibitory) signal on T cells, both of which result in amplifying antigen-specific T cell responses. Certain of the stimulatory and inhibitory molecules are members of the immunoglobulin super family (IgSF). One important family of membrane-bound ligands that bind to co-stimulatory or co-inhibitory receptors is the B7 family, which includes B7-1, B7-2, B7-H1 (PD-L1), B7-DC (PD-L2), B7-H2 (ICOS-L), B7-H3, B7-H4, B7-H5 (VISTA), and B7-H6. Another family of membrane bound ligands that bind to co-stimulatory or co-inhibitory receptors is the TNF family of molecules that bind to cognate TNF receptor family members, which includes CD40 and CD4OL, OX-40, OX-40L, CD70, CD27L, CD30, CD3OL, 4-1BBL, CD137 (4-1BB), TRAIL/Apo2-L, TRAILR1/DR4, TRAILR2/DR5, TRAILR3, TRAILR4, OPG, RANK, RANKL, TWEAKR/Fn14, TWEAK, BAFFR, EDAR, XEDAR, TACI, APRIL, BCMA, LT13R, LIGHT, DcR3, HVEM, VEGI/TL1A, TRAMP/DR3, EDAR, EDA1, XEDAR, EDA2, TNFR1, Lymphotoxin a/TNF13, TNFR2, TNFa, LT13R, Lymphotoxin a 1132, FAS, FASL, RELT, DR6, TROY, NGFR.

In another aspect, the immuno-oncology agent is a cytokine that inhibits T cell activation (e.g., IL-6, IL-10, TGF-B, VEGF, and other immunosuppressive cytokines) or a cytokine that stimulates T cell activation, for stimulating an immune response.

In one aspect, T cell responses can be stimulated by a combination of Compound I and one or more of (i) an antagonist of a protein that inhibits T cell activation (e.g., immune checkpoint inhibitors) such as CTLA-4, PD-1, PD-L1, PD-L2, LAG-3, TIM-3, Galectin 9, CEACAM-1, BTLA, CD69, Galectin-1, TIGIT, CD113, GPR56, VISTA, 2B4, CD48, GARP, PD1H, LAIR1, TIM-1, and TIM-4, and/or (ii) an agonist of a protein that stimulates T cell activation such as B7-1, B7-2, CD28, 4-1BB (CD137), 4-1BBL, ICOS, ICOS-L, OX40, OX4OL, GITR, GITRL, CD70, CD27, CD40, DR3 and CD2. Other agents that can be combined with Compound I for the treatment of cancer include antagonists of inhibitory receptors on NK cells or agonists of activating receptors on NK cells. For example, compounds herein can be combined with antagonists of KIR, such as lirilumab.

Yet other agents for combination therapies include agents that inhibit or deplete macrophages or monocytes, including but not limited to CSF-1R antagonists such as CSF-1R antagonist antibodies including RG7155 (WO11/70024, WO11/107553, WO11/131407, WO13/87699, WO13/119716, WO13/132044) or FPA-008 (WO11/140249; W013169264; WO14/036357).

In another aspect, Compound I can be used with one or more of agonistic agents that ligate positive costimulatory receptors, blocking agents that attenuate signaling through inhibitory receptors, antagonists, and one or more agents that increase systemically the frequency of anti-tumor T cells, agents that overcome distinct immune suppressive pathways within the tumor microenvironment (e.g., block inhibitory receptor engagement (e.g., PD-L1/PD-1 interactions), deplete or inhibit Tregs (e.g., using an anti-CD25 monoclonal antibody (e.g., daclizumab) or by ex vivo anti-CD25 bead depletion), or reverse/prevent T cell anergy or exhaustion) and agents that trigger innate immune activation and/or inflammation at tumor sites.

In one aspect, the immuno-oncology agent is a CTLA-4 antagonist, such as an antagonistic CTLA-4 antibody. Suitable CTLA-4 antibodies include, for example, YERVOY (ipilimumab) or tremelimumab.

In another aspect, the immuno-oncology agent is a PD-1 antagonist, such as an antagonistic PD-1 antibody. Suitable PD-1 antibodies include, for example, OPDIVO (nivolumab), KEYTRUDA (pembrolizumab), or MEDI-0680 (AMP-514; WO2012/145493). The immuno-oncology agent may also include pidilizumab (CT-011), though its specificity for PD-1 binding has been questioned. Another approach to target the PD-1 receptor is the recombinant protein composed of the extracellular domain of PD-L2 (B7-DC) fused to the Fc portion of IgGl, called AMP-224.

In another aspect, the immuno-oncology agent is a PD-L1 antagonist, such as an antagonistic PD-L1 antibody. Suitable PD-L1 antibodies include, for example, MPDL3280A (RG7446; WO2010/077634), durvalumab (MED14736), BMS-936559 (WO2007/005874), and MSB0010718C (W02013/79174).

In another aspect, the immuno-oncology agent is a LAG-3 antagonist, such as an antagonistic LAG-3 antibody. Suitable LAG3 antibodies include, for example, BMS-986016 (WO10/19570, WO14/08218), or IMP-731 or IMP-321 (WO08/132601, WO09/44273).

In another aspect, the immuno-oncology agent is a CD137 (4-1BB) agonist, such as an agonistic CD137 antibody. Suitable CD137 antibodies include, for example, urelumab and PF-05082566 (WO12/32433).

In another aspect, the immuno-oncology agent is a GITR agonist, such as an agonistic GITR antibody. Suitable GITR antibodies include, for example, BMS-986153, BMS-986156, TRX-518 (WO06/105021, WO09/009116) and MK-4166 (W011/028683).

In another aspect, the immuno-oncology agent is an OX40 agonist, such as an agonistic OX40 antibody. Suitable OX40 antibodies include, for example, MEDI-6383 or MEDI-6469.

In another aspect, the immuno-oncology agent is an OX4OL antagonist, such as an antagonistic OX40 antibody. Suitable OX4OL antagonists include, for example, RG-7888 (WO06/029879).

In another aspect, the immuno-oncology agent is a CD40 agonist, such as an agonistic CD40 antibody. In yet another embodiment, the immuno-oncology agent is a CD40 antagonist, such as an antagonistic CD40 antibody. Suitable CD40 antibodies include, for example, lucatumumab or dacetuzumab.

In another aspect, the immuno-oncology agent is a CD27 agonist, such as an agonistic CD27 antibody. Suitable CD27 antibodies include, for example, varlilumab.

In another aspect, the immuno-oncology agent is MGA271 (to B7H3) (WO11/109400).

The present invention encompasses pharmaceutically acceptable salts, acids or derivatives of any of the above.

Metabolic and Cardiovascular Diseases.

The present invention provides methods for treating and/or preventing certain cardiovascular- and/or metabolic-related diseases, disorders and conditions, as well as disorders associated therewith, with Compound I and at least one additional therapeutic or diagnostic agent.

Examples of therapeutic agents useful in combination therapy for the treatment of hypercholesterolemia (and atherosclerosis as well) include statins (e.g., CRESTOR, LESCOL, LIPITOR, MEVACOR, PRAVACOL, and ZOCOR), which inhibit the enzymatic synthesis of cholesterol; bile acid resins (e.g., COLESTID, LO-CHOLEST, PREVALITE, QUESTRAN, and WELCHOL), which sequester cholesterol and prevent its absorption; ezetimibe (ZETIA), which blocks cholesterol absorption; fibric acid (e.g., TRICOR), which reduces triglycerides and may modestly increase HDL; niacin (e.g., NIACOR), which modestly lowers LDL cholesterol and triglycerides; and/or a combination of the aforementioned (e.g., VYTORIN (ezetimibe with simvastatin). Alternative cholesterol treatments that may be candidates for use in combination with Compound I include various supplements and herbs (e.g., garlic, policosanol, and guggul).

The present invention encompasses pharmaceutically acceptable salts, acids or derivatives of any of the above.

Immune- and Inflammatory-Related Disorders.

The present invention provides methods for treating and/or preventing immune-related diseases, disorders and conditions; and diseases, disorders and conditions having an inflammatory component; with Compound I and at least one additional therapeutic or diagnostic agent.

Examples of therapeutic agents useful in combination therapy include, but are not limited to, the following: non-steroidal anti-inflammatory drug (NSAID) such as aspirin, ibuprofen, and other propionic acid derivatives (alminoprofen, benoxaprofen, bucloxic acid, carprofen, fenbufen, fenoprofen, fluprofen, flurbiprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, fuirofenac, ibufenac, isoxepac, oxpinac, sulindac, tiopinac, tolmetin, zidometacin, and zomepirac), fenamic acid derivatives (flufenamic acid, meclofenamic acid, mefenamic acid, niflumic acid and tolfenamic acid), biphenylcarboxylic acid derivatives (diflunisal and flufenisal), oxicams (isoxicam, piroxicam, sudoxicam and tenoxican), salicylates (acetyl salicylic acid, sulfasalazine) and the pyrazolones (apazone, bezpiperylon, feprazone, mofebutazone, oxyphenbutazone, phenylbutazone). Other combinations include cyclooxygenase-2 (COX-2) inhibitors.

Other active agents for combination include steroids such as prednisolone, prednisone, methylprednisolone, betamethasone, dexamethasone, or hydrocortisone. Such a combination may be especially advantageous since one or more adverse effects of the steroid can be reduced or even eliminated by tapering the steroid dose required.

Additional examples of active agents that may be used in combinations for treating, for example, rheumatoid arthritis, include cytokine suppressive anti-inflammatory drug(s) (CSAIDs); antibodies to, or antagonists of, other human cytokines or growth factors, for example, TNF, LT, IL-10, IL-2, IL-6, IL-7, IL-8, IL-15, IL-16, IL-18, EMAP-II, GM-CSF, FGF, or PDGF.

Particular combinations of active agents may interfere at different points in the autoimmune and subsequent inflammatory cascade, and include TNF antagonists such as chimeric, humanized or human TNF antibodies, REMICADE, anti-TNF antibody fragments (e.g., CDP870), and soluble p55 or p75 TNF receptors, derivatives thereof, p75TNFRIgG (ENBREL.) or p55TNFR1gG (LENERCEPT), soluble IL-13 receptor (sIL-13), and also TNFa-converting enzyme (TACE) inhibitors; similarly, IL-1 inhibitors (e.g., Interleukin-1-converting enzyme inhibitors) may be effective. Other combinations include Interleukin 11, anti-P7s and p-selectin glycoprotein ligand (PSGL). Other examples of agents useful in combination with the Compound I include interferon-131a (AVONEX); interferon-131b (BETASERON); copaxone; hyperbaric oxygen; intravenous immunoglobulin; clabribine; and antibodies to, or antagonists of, other human cytokines or growth factors (e.g., antibodies to CD40 ligand and CD80).

Microbial Diseases.

The present invention provides methods for treating and/or preventing viral, bacterial, fungal and parasitic diseases, disorders and conditions, as well as disorders associated therewith, with Compound I and at least one additional therapeutic or diagnostic agent (e.g., one or more other antiviral agents and/or one or more agents not associated with viral therapy).

Such combination therapy includes anti-viral agents targeting various viral life-cycle stages and having different mechanisms of action, including, but not limiting to, the following: inhibitors of viral uncoating (e.g., amantadine and rimantidine); reverse transcriptase inhibitors (e.g., acyclovir, zidovudine, and lamivudine); agents that target integrase; agents that block attachment of transcription factors to viral DNA; agents (e.g., antisense molecules) that impact translation (e.g., fomivirsen); agents that modulate translation/ribozyme function; protease inhibitors; viral assembly modulators (e.g., rifampicin); antiretrovirals such as, for example, nucleoside analogue reverse transcriptase inhibitors (e.g., azidothymidine (AZT), ddI, ddC, 3TC, d4T); non-nucleoside reverse transcriptase inhibitors (e.g., efavirenz, nevirapine); nucleotide analogue reverse transcriptase inhibitors; and agents that prevent release of viral particles (e.g., zanamivir and oseltamivir). Treatment and/or prevention of certain viral infections (e.g., HIV) frequently entail a group ("cocktail") of antiviral agents.

Other antiviral agents contemplated for use in combination with Compound I include, but are not limited to, the following: abacavir, adefovir, amantadine, amprenavir, ampligen, arbidol, atazanavir, atripla, boceprevirertet, cidofovir, combivir, darunavir, delavirdine, didanosine, docosanol, edoxudine, emtricitabine, enfuvirtide, entecavir, famciclovir, fosamprenavir, foscarnet, fosfonet, http://en.wikipedia.org/wiki/Fusion_inhibitor ganciclovir, ibacitabine, imunovir, idoxuridine, imiquimod, indinavir, inosine, various interferons (e.g., peginterferon alfa-2a), lopinavir, loviride, maraviroc, moroxydine, methisazone, nelfinavir, nexavir, penciclovir, peramivir, pleconaril, podophyllotoxin, raltegravir, ribavirin, ritonavir, pyramidine, saquinavir, stavudine, telaprevir, tenofovir, tipranavir, trifluridine, trizivir, tromantadine, truvada, valaciclovir, valganciclovir, vicriviroc, vidarabine, viramidine, and zalcitabine.

The present invention contemplates the use of the inhibitors of $A_{2A}R/A_{2B}R$ function described herein in combination with antiparasitic agents. Such agents include, but are not limited to, thiabendazole, pyrantel pamoate, mebendazole, praziquantel, niclosamide, bithionol, oxamniquine, metrifonate, ivermectin, albendazole, eflornithine, melarsoprol, pentamidine, benznidazole, nifurtimox, and nitroimidazole. The skilled artisan is aware of other agents that may find utility for the treatment of parasitic disorders.

Embodiments of the present invention contemplate the use of Compound I in combination with agents useful in the treatment or prevention of bacterial disorders. Antibacterial agents can be classified in various manners, including based on mechanism of action, based on chemical structure, and based on spectrum of activity. Examples of antibacterial agents include those that target the bacterial cell wall (e.g., cephalosporins and penicillins) or the cell membrane (e.g., polymyxins), or interfere with essential bacterial enzymes (e.g., sulfonamides, rifamycins, and quinolines). Most antibacterial agents that target protein synthesis (e.g., tetracyclines and macrolides) are bacteriostatic, whereas agents such as the aminoglycoside are bactericidal. Another means of categorizing antibacterial agents is based on their target specificity; "narrow-spectrum" agents target specific types of bacteria (e.g., Gram-positive bacteria such as *Streptococcus*), while "broad-spectrum" agents have activity against a broader range of bacteria. The skilled artisan is aware of types of antibacterial agents that are appropriate for use in specific bacterial infections.

Embodiments of the present invention contemplate the use of Compound I in combination with agents useful in the treatment or prevention of fungal disorders. Antifungal agents include polyenes (e.g., amphotericin, nystatin, and pimaricin); azoles (e.g., fluconazole, itraconazole, and ketoconazole); allylamines (e.g., naftifine, and terbinafine) and morpholines (e.g., amorolfine); and antimetabolies (e.g., 5-fluorocytosine).

The present invention encompasses pharmaceutically acceptable salts, acids or derivatives of the agents (and members of the classes of agents) set forth above.

Kits

Also provided herein are kits comprising a pharmaceutical composition and dosage form of Compound I, and pharmaceutical compositions thereof. The kits are generally in the form of a physical structure housing various components, as described below, and may be utilized, for example, in practicing the methods described above.

When combination therapy is contemplated, the kit may contain the several agents separately or they may already be combined in the kit. Each component of the kit may be enclosed within an individual container, and all of the various containers may be within a single package. A kit of the present invention may be designed for conditions necessary to properly maintain the components housed therein (e.g., refrigeration or freezing).

A kit may contain a label or packaging insert including identifying information for the components therein and instructions for their use (e.g., dosing parameters, clinical pharmacology of the active ingredient(s), including mechanism of action, pharmacokinetics and pharmacodynamics, adverse effects, contraindications, etc.). Labels or inserts can include manufacturer information such as lot numbers and expiration dates. The label or packaging insert may be, e.g., integrated into the physical structure housing the components, contained separately within the physical structure, or affixed to a component of the kit (e.g., an ampule, tube or vial).

Labels or inserts can additionally include, or be incorporated into, a computer readable medium, such as a disk (e.g., hard disk, card, memory disk), optical disk such as CD- or DVD-ROM/RAM, DVD, MP3, magnetic tape, or an electrical storage media such as RAM and ROM or hybrids of these such as magnetic/optical storage media, FLASH media or memory-type cards. In some embodiments, the actual instructions are not present in the kit, but means for obtaining the instructions from a remote source, e.g., via the internet, are provided.

EXPERIMENTAL

The following examples are put forth so as to provide those of ordinary skill in the art with a complete disclosure and description of how to make and use the present invention, and are not intended to limit the scope of what the inventors regard as their invention, nor are they intended to represent that the experiments below were performed or that they are all of the experiments that may be performed. It is to be understood that exemplary descriptions written in the present tense were not necessarily performed, but rather that the descriptions can be performed to generate data and the like of a nature described therein. Efforts have been made to ensure accuracy with respect to numbers used (e.g., amounts, temperature, etc.), but some experimental errors and deviations should be accounted for.

Unless indicated otherwise, parts are parts by weight, molecular weight is weight average molecular weight, temperature is in degrees Celsius (° C.), and pressure is at or near atmospheric. Standard abbreviations are used, including the following: wt=wildtype; bp=base pair(s); kb= kilobase(s); nt=nucleotides(s); as =amino acid(s); s or sec= second(s); min=minute(s); h or hr=hour(s); ng=nanogram; μg=microgram; mg=milligram; g=gram; kg=kilogram; dl or dL=deciliter; pl or 1AL=microliter; ml or mL=milliliter; l or L=liter; μM=micromolar; mM=millimolar; M=molar; kDa=kilodalton; i.m.=intramuscular(ly); i.p.=intraperitoneal (ly); SC or SQ=subcutaneous(ly); QD=daily; BID=twice daily; QW=weekly; QM=monthly; HPLC=high performance liquid chromatography; BW=body weight; U=unit; ns=not statistically significant; PBS=phosphate-buffered saline; IHC=immunohistochemistry; DMEM=Dulbeco's Modification of Eagle's Medium; EDTA=ethylenediaminetetraacetic acid.

Materials and Methods

The following general materials and methods were used, where indicated, or may be used in the Examples below:

Standard methods in molecular biology are described in the scientific literature (see, e.g., Sambrook and Russell (2001) Molecular Cloning, 3rd ed., Cold Spring Harbor Laboratory Press, Cold Spring Harbor, N.Y.; and Ausubel, et al. (2001) Current Protocols in Molecular Biology, Vols. 1-4, John Wiley and Sons, Inc. New York, N.Y., which describes cloning in bacterial cells and DNA mutagenesis (Vol. 1), cloning in mammalian cells and yeast (Vol. 2), glycoconjugates and protein expression (Vol. 3), and bioinformatics (Vol. 4)).

The scientific literature describes methods for protein purification, including immunoprecipitation, chromatography, electrophoresis, centrifugation, and crystallization, as well as chemical analysis, chemical modification, post-translational modification, production of fusion proteins, and glycosylation of proteins (see, e.g., Coligan, et al. (2000) Current Protocols in Protein Science, Vols. 1-2, John Wiley and Sons, Inc., NY).

Software packages and databases for determining, e.g., antigenic fragments, leader sequences, protein folding, functional domains, glycosylation sites, and sequence alignments, are available (see, e.g., GCG Wisconsin Package (Accelrys, Inc., San Diego, Calif.); and DeCypher™ (TimeLogic Corp., Crystal Bay, Nev.).

The literature is replete with assays and other experimental techniques that can serve as a basis for evaluation of the compounds described herein.

EXAMPLES

Example 1: Synthesis of 3-[2-amino-6-(1-{[6-(2-hydroxypropan-2-yl)pyridin-2-yl]methyl}-1H-1,2,3-triazol-4-yl)pyrimidin-4-yl]-2-methylbenzonitrile

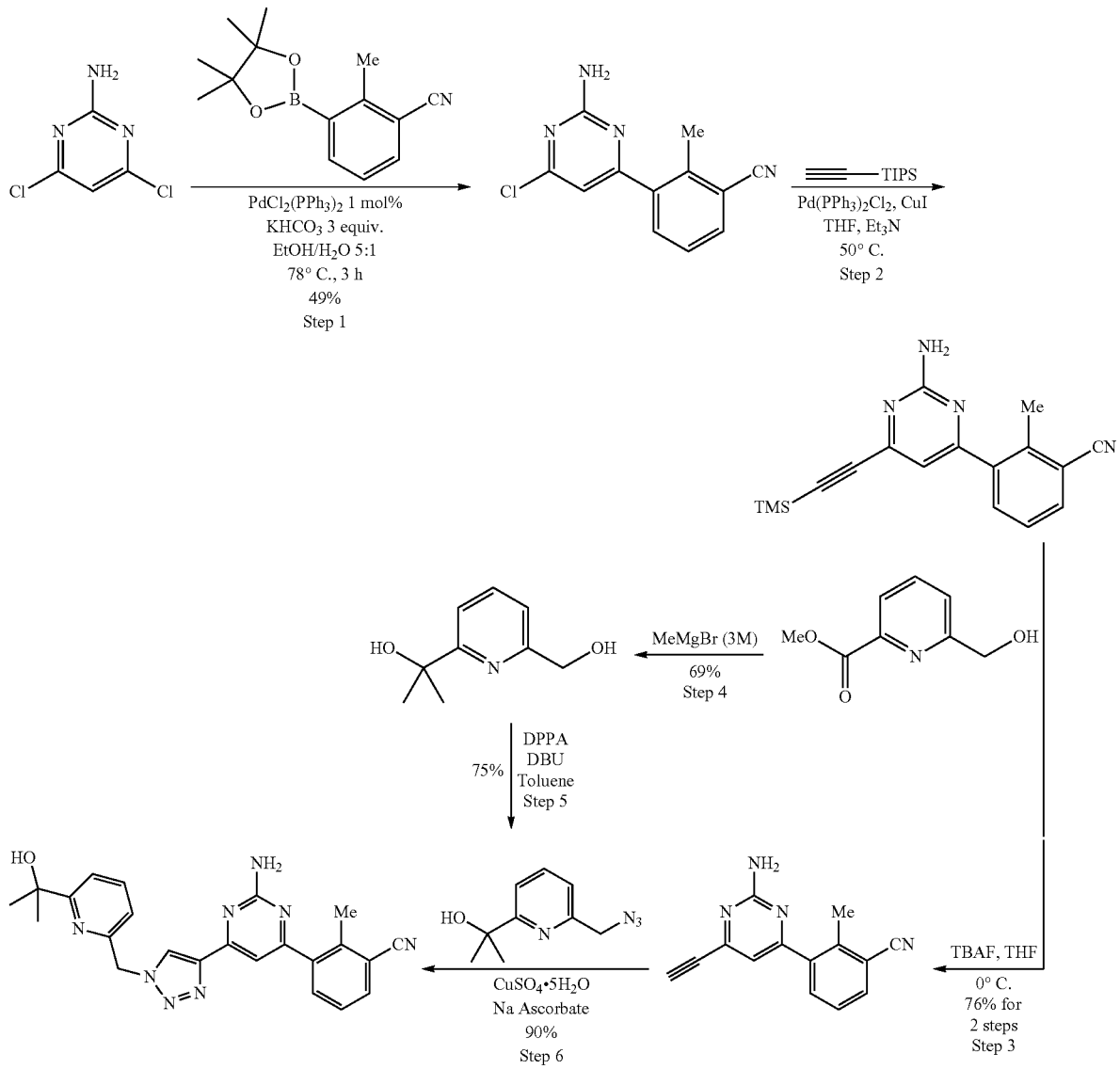

Step 1:

In a 250 mL round bottom flask equipped with a magnetic stir bar was successively charged the boronic ester (3.89 g, 16 mmol) and the 2-amino-4,6-dichloropyrimidine (3.67 g, 22.4 mmol). Absolute ethanol (100 mL) was added followed by a solution of $KHCO_3$ (4.81 g, 48 mmol) in deionized water (19 mL). The resulting suspension was degassed with nitrogen for 5 minutes. $PdCl_2(PPh_3)_2$ (112 mg, 1 mol %) was then added and the mixture was heated to 78° C. for 3 hours under a nitrogen atmosphere. Ethanol was evaporated under reduced pressure and deionized water (150 mL) was added. The suspension was filtered and the solid was washed with additional water (100 mL). The solid was then dissolved in acetone (220 mL) and collected in a 500 mL round bottom flask. A mixture of silica and celite (1:1, 150 g) was added and the solvent was removed under reduced pressure. The resulting crude material was purified by flash chromatography over silica gel (dichloromethane/ethyl acetate gradient 0% to 15%). The desired product was obtained as a white solid (1.91 g, 49%). LCMS: Method A, retention time=2.93 min, ESI MS [M+H]$^+$ for $C_{12}H_9ClN_4$, calcd 245.7. found 245.2.

Step 2:

In a round-bottom flask 5.1 g (20.8 mmol) of chloropyrimidine was suspended in 42 mL of degassed THF. To this suspension was added 8.68 mL (62.4 mmol) of $Et_3N$ and 5.95 mL (25.0 mmol) of TIPS-acetylene. The reaction mixture was stirred for 5 min, followed by addition of 219 mg (0.312 mmol) of $PdCl_2(PPh_3)_2$ and 119 mg (0.624 mmol) of CuI. The reaction mixture was stirred at 50° C. for 5 h under N$_2$. After cooling the reaction to room temp., solvent was removed and the crude material was resuspended in 100 mL EtOAc from which insoluble solid was filtered off. The filtrate was washed with (1:1) NH$_4$Cl/NH$_4$OH (2×100 mL) and 10% Na$_2$S$_2$O$_4$ (1×100 mL). The organic layer was dried using Na$_2$SO$_4$, concentrated and taken to next step without further purification.

Step 3:

In a round-bottom flask the crude TIPS product from previous step was dissolved in 42 mL dry THF and cooled to 0° C. To this was added 25 mL (25.0 mmol) of TBAF (1.0 M in THF). The reaction was stirred at 0° C. for 15 min. Saturated NH$_4$Cl (100 mL) was added to quench the reaction. The organics were extracted from the aqueous layer with EtOAc (2×100 mL). The combined organic layer was washed with (1:1) NH$_4$Cl/NH$_4$OH (2×100 mL) and 10% Na$_2$S$_2$O$_4$ (1×100 mL). The organic layer was dried using Na$_2$SO$_4$, concentrated and the pure product 5 was obtained by triturating with 40% CH$_2$Cl$_2$/Hexane as a light brown solid. Yield: 3.71 g (76%, 2-steps).

Step 4:

To a solution of methylmagnesium bromide (3 M in Et$_2$O, 40 mL, 120 mmol, 4.0 equiv) at 0° C. under N$_2$ was added a solution of methyl 2-(hydroxymethyl)pyridine-2-carboxylate (5.0 g, 29.9 mmol) in THF (70 mL, 0.4 M) over the course of 30 minutes. The resulting mixture was allowed to warm to room temperature and stirred for 3 h. The reaction mixture was quenched with NH$_4$Cl aq (55 mL) and EtOAc (50 mL) was added. The organic phase was separated, and the aqueous phase was extracted with EtOAc (3×40 mL). The combined organic extracts were washed with saturated aqueous sodium bisulfite (7×20 mL), then dried (Na$_2$SO$_4$), filtered and concentrated in vacuo to give the title compound (3.45 g, 69% yield; 96% purity as judged by LCMS) as a pale yellow liquid. LCMS: Method A, retention time=0.722 and 1.06 min, ESI MS [M+H]$^+$ for C$_9$H$_{13}$NO$_2$, calcd 167.09. found 167.2.

Step 5:

To a solution of 2-hydroxymethyl-6-(1-hydroxy-1-methylethyl)pyridine (5 g, 29.9 mmol, 1.0 equiv) in PhMe (33 mL, 0.9M) at 0° C. under N$_2$ was added diphenylphosphoryl azide (7.73 mL, 35.9 mmol, 1.2 equiv.), followed by 1,8-diazabicyclo[5.4.0]undec-7-ene (5.37 mL, 35.9 mmol, 1.2 equiv.). The resulting mixture was to warm to room temperature and stirred for 14 h. Upon completion, diluted with ethyl acetate and washed with water, the organic layer was dried (Na$_2$SO$_4$), filtered and concentrated. The residue was dissolved in 1N aq HCl (2 eq, 60 mmol) and extracted with MTBE in hexanes (3:7, 100 mL), the organic layer was washed with water (50 mL) and the combined aqueous layer was neutralized with 2N aqueous NaOH and extracted with ethyl acetate (3×75 mL), dried the organic layer (Na$_2$SO$_4$), filtered through a plug of cotton and concentrated the filtrate to afford the pure compound as pale yellow color liquid (3.75 g, 75%). LCMS: Method A, retention time=2.67 min, ESI MS [M+H]$^+$ for C$_9$H$_{12}$N$_4$O, calcd 193.1. found 193.2.

Step 6:

A mixture of azide (3.34 g, 17.4 mmol), alkyne (3.71 g, 15.8 mmol), copper(II) sulfate (39 mg; 0.158 mmol), and sodium ascorbate (156 mg, 0.790 mmol) in 2:1 t-BuOH/H$_2$O (158 mL) was heated at 60° C. for 13 h. The solvent was removed in vacuo, the residue dry loaded onto silica gel, and purified by silica gel chromatography (0-100% EtOAc in hexanes) to afford the desired product as an off-white solid (6.08 g, 90%). $^1$H NMR (400 MHz, DMSO-d$_6$) δ 8.69 (s, 1H), 7.90 (d, J=7.8 Hz, 1H), 7.80 (t, J=7.8 Hz, 1H), 7.76 (d, J=7.8 Hz, 1H), 7.61 (d, J=8.0 Hz, 1H), 7.51 (t, J=7.8 Hz, 1H), 7.28 (s, 1H), 7.10 (d, J=7.6 Hz, 2H), 6.90 (s, 2H), 5.81 (s, 2H), 5.23 (s, 1H), 2.55 (s, 3H), 1.38 (s, 6H). ESI MS [M+H]$^+$ for C$_{23}$H$_{23}$N$_8$O, calcd 427.2. found 427.3.

Example 2: Single Ascending Dose (SAD) Study & Multiple Ascending Dose (MAD) Study This is a double-blind, randomized, placebo-controlled combined single ascending dose (SAD) and multiple ascending dose (MAD) study that includes an additional food effect (FE) study.

Healthy participants have been chosen as the study population given the study design, low risk of clinically significant toxicity at anticipated exposure levels, and sufficiently short duration of exposure that will not be able to provide clear therapeutic benefit and justify patients discontinuing current therapies. Moreover, use of healthy participants as opposed to patients will allow clearer interpretation of the study results, as there will be no confounding factors resulting from changes in disease state and/or concomitant medications.

The SAD part consists of 5 groups of 8 healthy young male and female participants, gender balanced to the extent possible, receiving a single oral dose in Groups 1 to 4 or 2 doses in Group 5 of Compound I or placebo (randomized 3:1, active vs placebo, respectively). All participants in the SAD portion of the study must be fasting prior to receiving Compound I. All groups will be evaluated based on pharmacokinetic (PK), safety and tolerability prior to escalation to the next highest group or starting the MAD portion of the study.

Participants will be replaced if they do not receive all assigned doses. The replacement participant will be assigned to the same dose level and drug product (or placebo) as the original participant.

The MAD part may start once a sufficient number of cohorts in the SAD portion of the study have been completed. The MAD part consists of 5 groups of 8 healthy young male and female participants, gender balanced to the extent possible, each receiving oral doses of Compound I or placebo (randomized 3:1, active vs placebo, respectively) once daily (qd) for 4 days in Groups 1 to 4 or every 12 hours (q12 h) for 4 days in Group 5. The MAD part of the study will be escalated based on evaluation of PK, safety, and tolerability.

The FE part of the study may start once there is a decision to start the MAD part of the study, and will consist of 1 group of 3 to 6 participants at a selected dose based on data from the SAD and available MAD parts of the study. The FE participants will fast for the first dose of Compound I on Day 1. After a brief wash-out period, the participants will receive the second dose of Compound I after food on Day 7, for a total of 2 doses of Compound I.

This dosing schedule may change depending on the PK in the SAD portion of the study. The dose for the FE part will be one of the doses from Groups 1 to 4.

Although this is a dose escalation study, if unacceptable results for safety or tolerability are experienced or depending on the PK results from prior cohorts, not all portions of the study may be conducted or lower doses may be administered in the next groups. Further, the same dose may be tested in two groups, an intermediate dose may be tested to gain more information on safety, tolerability and/or PK or dosing may change from qd to twice per day.

Dose levels to be evaluated in SAD/expected dose levels in MAD:

Group 1: 10 mg Compound I (n=6) or matching placebo (n=2)
Group 2: 25 mg Compound I (n=6) or matching placebo (n=2)
Group 3: 75 mg Compound I (n=6) or matching placebo (n=2)
Group 4: 150 mg Compound I (n=6) or matching placebo (n=2)
Group 5: 200 mg Compound I (n=6) or matching placebo (n=2)

In Groups 1 to 4, Compound I or placebo will be administered once for SAD and qd for MAD. In Group 5, Compound I or placebo will be administered at 100 mg q12 h for SAD and at 200 mg (fed) for MAD.

SAD part: Escalation to the next higher dose will be based on available safety and PK (and pharmacodynamics (PD) if available) data from the prior dose groups as well as data from the group being evaluated. Dosing will be done in a fasted state.

MAD part: Escalation to the next higher dose and any dose adjustments of the next dose levels will be determined after evaluation of the PK, safety and tolerability of previous MAD (when applicable) dose groups. The MAD part may start during the SAD part, but only when the first 3 groups of SAD data are available. The MAD starting dose will be 10 mg. Participants in MAD will receive multiple doses of Compound I or matching placebo qd (Groups 1 to 4) or q12 h (Group 5) from Day 1 to Day 4 in a fasted state.

FE part: The FE study will be decided once the MAD portion of the study can be started. The Compound I dose will be decided based on SAD and available MAD data. Compound I will be administered in one period under fasting conditions and after a high-fat breakfast in the other period for the FE study.

Study Design

The current study design was chosen based on the current study population, and non-clinical and available external data. An escalating-dose study design was chosen for the SAD and MAD parts to allow careful increase of the dose after assessment of safety and tolerability, and PK of each preceding dose. Dose escalation will be guided by safety and tolerability and PK analysis of the participants in a dose group following a minimum of 48 hours post-dose observation period. Dose escalation will be performed when none of the stop criteria have been reached (see below).

Stopping Rules for Dose Escalation

Stopping dose escalation, for each participant and/or within each cohort, will be considered if any of the following specific scenarios occur with a reasonable possibility of a causal relationship with the study medication:

One or more participants report a serious adverse event (SAE) or experience severe AEs, including labs that are clinically significant.

In addition, the sponsor and investigator may decide to halt dose escalation for reasons not defined above, including but not limited to, observing a single SAE in individual subjects and/or observing trends in a given dose cohort and across dose cohorts.

Other findings that, at the discretion of the sponsor and investigator, indicate that further dosing should be stopped.

Food Effect

Participants will receive the same single dose of Compound I in 2 treatment periods. The first treatment period will be conducted under fasted conditions and the second treatment period will be conducted under fed conditions to study a possible effect of food on the PK of Compound I.

Selection of Study Population—Inclusion Criteria

The following inclusion criteria must be met for a participant to be eligible for inclusion in the study:

1. Male or female participants aged 18 to 55 years, inclusive;
2. Willing and able to sign informed consent;
3. Body mass index (BMI) between 19 and 30 kg/m$^2$ inclusive;
4. Healthy as determined by pre-study medical history, physical examination, vital signs, complete neurological examination and 12-lead ECG;
5. Negative tests for hepatitis B surface antigen (HBsAg), anti-hepatitis C virus (HCV), and human immunodeficiency virus (HIV)-1 and HIV-2 antibody at screening;
6. All clinical laboratory tests of blood and urine must be within the normal range or show no clinically relevant deviations as judged by the PI at screening and admission;
7. Non-smokers or ex-smokers who have ceased smoking >3 months prior to screening visit;
8. In case of inclusion of females of childbearing potential, females of non-childbearing potential and postmenopausal females: At screening, females must be non-pregnant and non-lactating, or of non-childbearing potential (either surgically sterilized or physiologically incapable of becoming pregnant, or at least 1 year post-menopausal [amenorrhoea duration of 12 consecutive months]) confirmed by follicle-stimulating hormone testing; non-pregnancy will be confirmed for all females by a serum pregnancy test conducted at screening, and a urine or serum pregnancy test at each admission;
9. Female participants of child-bearing potential, with a fertile male sexual partner, must agree to use adequate contraception from screening until 90 days after the follow-up visit. Adequate contraception is defined as using hormonal contraceptives or an intrauterine device combined with at least 1 of the following forms of contraception: a diaphragm or cervical cap, or a condom. Also, total abstinence, in accordance with the lifestyle of the participant, is acceptable;
10. Male participants, if not surgically sterilized, must agree to use adequate contraception and not donate sperm from (first) admission to the clinical research center until 90 days after the follow-up visit. Adequate contraception for the male participant (and his female partner) is defined as using hormonal contraceptives or an intrauterine device combined with at least 1 of the following forms of contraception: a diaphragm or cervical cap, or a condom. Also, total abstinence, in accordance with the lifestyle of the participant is acceptable;
11. All prescribed medication must have been stopped at least 30 days prior to (each) admission to the clinical research center. An exception is made for hormonal contraceptives, which may be used throughout the study;
12. All over-the-counter medication, vitamin preparations and other food supplements, or herbal medications (eg, St. John's Wort) must have been stopped at least 14 days prior to (each) admission to the clinical research center. An exception is made for paracetamol, which is allowed up to admission to the clinical research center;
13. Ability and willingness to abstain from alcohol, methylxanthine-containing beverages or food (coffee, tea, cola, chocolate, energy drinks), and grapefruit (juice) and tobacco products from 48 hours prior to (each) admission to and during the stay in the clinical research center.

Selection of Study Population—Exclusion Criteria

A participant who meets any of the following exclusion criteria will not be eligible for inclusion in the study:
1. Previous participation in the current study;
2. History of relevant drug and/or food allergies;
3. History of alcohol abuse or drug addiction (including soft drugs like *cannabis* products);
4. Positive drug and alcohol screen (opiates, methadone, cocaine, amphetamines [including ecstasy], cannabinoids, barbiturates, benzodiazepines, gamma-hydroxybutyric acid, tricyclic antidepressants and alcohol) at screening and (each) admission to the clinical research center;
5. Average intake of more than 24 units of alcohol per week (1 unit of alcohol equals approximately 250 mL of beer, 100 mL of wine or 35 mL of spirits);
6. Participation in a drug study within 60 days prior to (the first) drug administration in the current study. Participation in more than 4 other drug studies in the 12 months prior to (the first) drug administration in the current study;
7. Donation or loss of more than 100 mL of blood within 60 days prior to (the first) drug administration. Donation or loss of more than 1.5 L of blood (for male participants)/more than 1.0 L of blood (for female participants) in the 10 months prior to (the first) drug administration in the current study;
8. Non-willingness to consume the Food and Drug Administration (FDA) breakfast (applicable to the FE part);
9. Unsuitable veins for blood sampling;
10. Participants who have a clinically relevant history or presence of respiratory, gastrointestinal, renal, hepatic, hematological, lymphatic, neurological, cardiovascular, psychiatric, musculoskeletal, genitourinary, immunological, dermatological, endocrine, connective tissue diseases or disorders;
11. Have a significant infection or known inflammatory process on screening or admission.

Please note that participants should refrain from consumption of any foods containing poppy seeds within 48 hours (2 days) prior to screening and first admission to the clinical research center to avoid false positive drug screen results. In addition, they should refrain from strenuous exercise within 96 hours (4 days) prior to screening and first admission as this could result in abnormal clinical laboratory values.

Timing of Doses in the Study

Dosing Under Fasted Conditions:

For Groups 1 to 4, the study drug will be administered with the participant in the upright position. Study drug will be administered to participants between 08:00 and 9:00 hours in the morning. Before the morning dose, participants will be fasted overnight for at least 10 hours following a light supper on the evening before. Within a period, dosing should be at the same time each day 15 minutes. The study drug will be swallowed together with 240 mL tap water. The study drug should not be chewed. Fasting will continue for a period of 4 hours after drug administration. During fasting, no fluids are allowed except water; however, water is not allowed from 2 hours pre-dose until 1 hour post-dose. When not fasting, non-caffeinated fluids are allowed ad libitum.

For Group 5, the study drug will be administered with the participant in the upright position. The morning dose of study drug will be administered to participants between 08:00 and 9:00 hours in the morning. Before the morning dose, participants will be fasted overnight for at least 8 hours following a light supper on the evening before. Within a period, dosing should be at the same time each day 15 minutes. For the evening dose participants should be fasting for 2 hours prior to study drug administration. The study drug will be swallowed together with 240 mL tap water. The study drug should not be chewed. Fasting will continue for a period of 2 hours after drug administration. During fasting, no fluids are allowed except water; however, water is not allowed from 2 hours pre-dose until 1 hour post-dose. When not fasting, non-caffeinated fluids are allowed ad libitum.

Dosing Under Fed Conditions

The study drug will be administered with the participant in the upright position. Study drug will be administered to participants between 08:00 and 9:00 hours in the morning. After an overnight fast of at least 10 hours, participants will receive a standardized/FDA high-fat breakfast which will have to be finished within 20 minutes. The entire breakfast must be consumed by the participants. Dosing will occur at 30 minutes after the start of breakfast. The study drug will be swallowed together with 240 mL tap water. The study drug should not be chewed. Following drug administration participants will fast for a period of 4 hours until lunch. During fasting, no fluids are allowed except water.

Meals During the Study

A fasting period of at least 4 hours is required before obtaining clinical laboratory samples at all time points, thus at screening, (each) admission, and follow-up.

With the exception of the restrictions with respect to methylxanthine and alcohol containing beverages or food, there are no special requirements related to food and beverage intake. When not fasting, meals and snacks (such as decaffeinated coffee, herbal tea, fruit, biscuits) will be provided. A light supper will be provided on the evening before those days where fasting is required until lunch-time.

The FDA high-fat breakfast of 918 kcal consists of:
2 fried eggs (in 15 g butter/margarine) (approximately 100 g)
1 portion of bacon (40 g)*
  * For vegetarians bacon may be replaced by brie 60+
1 portion of fried potatoes (115 g)
2 slices of (toasted) (wheat) bread with 15 g margarine
1 glass of high fat milk (240 mL)

Pharmacokinetic, Pharmacodynamic, and Safety Measurements Assessed and Schedule of Assessments Schedules of assessments are presented in Table 1, Table 2, and Table 3.

TABLE 1

Schedule of Assessments—Single Ascending Dose

| Visit | Screening | Admission | Confinement | | | Discharge | Follow-up |
|---|---|---|---|---|---|---|---|
| Study Day | −28 to −2 | −1 | 1 | 2 | 3 | | 7 to 10 [15] |
| Written informed consent | X | | | | | | |
| Medical history | X | | | | | | |
| Medical history update | | X | | | | | X |
| Physical examination [1] | X | X | | | | | X |
| Neurological examination [2] | X | X | X | X | X | | X |
| VAS/DSST [3] | | X | X | X | | | |
| EEG [4] | X | | | | | | |

TABLE 1-continued

Schedule of Assessments—Single Ascending Dose

| Visit | Screening | Admission | Confinement | | | Discharge | Follow-up |
|---|---|---|---|---|---|---|---|
| Study Day | −28 to −2 | −1 | 1 | 2 | 3 | | 7 to 10 [15] |
| Vital signs [5] | X | X | X | X | X | | X |
| 12-lead ECG [6] | X | X | X | X | X | | X |
| Viral serology | X | | | | | | |
| ETOH and drug screen | X | X | | | | | |
| Hematology | X | X | | | X | | X |
| Chemistry | X | X | | | X | | X |
| Coagulation | X | X | | | X | | X |
| Urinalysis | X | X | | | X | | X |
| Cumulative urine collection (PK, metabolites) [7] | | | X | X | X | | X |
| Serum pregnancy test [8] | X | | | | | | |
| Serum or urine pregnancy test [8] | | X | | | | | |
| Hormone panel (FSH testing) [9] | X | | | | | | |
| Eligibility criteria review | X | | X [10] | | | | |
| Randomisation [10] | | | X | | | | |
| PK blood draw [11] | | | X | X | X | | |
| PD blood draw [12] | | | X | X | | | |
| Telemetry [13] | | | X | X | | | |
| Study drug administration | | | X | | | | |
| Adverse event monitoring [14] | X | X | X | X | X | | X |

Table 1 notes:
[1] A complete physical examination will be performed at screening (height and weight included at screening only). A physical examination update will be performed on Day −1 and at follow-up.
[2] Neurological examination consists of a clinical evaluation and Body Sway test. A full neurological examination will be performed at screening, Day −1, and at follow-up. An abbreviated exam consisting of a clinical examination (targeted), Body Sway test, and indication-specific examination will be performed on all other days.
[3] Bond and Lader VAS of Mood and Alertness; DSST; training DSST and first test on Day −1, on Days 1 and 2 DSST in time window of 2-4 hours post-dose for Groups 1 to 4, and on Day 1 in time window of 2-4 hours post-dose for Group 5.
[4] EEG will be performed at screening for participants receiving doses higher than 75 mg (ie, Groups 3 and higher) and if clinically indicated for any neurological adverse events during the study.
[5] Vital signs consist of blood pressure, pulse rate, body temperature, and respiratory rate. Supine and standing vital signs are to be performed in triplicate at screening and Day −1. Single supine and standing vital signs will be collected on Day 1 pre-dose and 1, 2, 3, 4, 6, 8, 12, and 48 hours post-dose for Groups 1-4. For Group 5 (2 doses), vitals will be collected on Day 1 pre-dose, 1, 2, 3, 4, 5, 6, 8, 24 and 48 hours after the first dose and pre-dose, 1, 2, and 3 hours after the second dose. Vitals should be collected at follow-up for all groups.
[6] ECG will be collected in triplicate at all time points. Participants should be least 15 minutes in supine position before each triplicate ECG. ECGs should be collected before each PK sample if PK sample is at the same timepoint. ECGs will be collected at screening and Day −1 on admission and 2, 4, and 8 hours after admission. ECGs will be collected pre-dose and 0.5, 1, 2, 3, 4, 6, 8, 12, 24, and 48 hours post-dose (and other days if clinically indicated) for Groups 1 to 4. For Group 5 (2 doses), ECG should be collected on Day 1 pre-dose, 0.5, 1, 2, 3, 4, 5, 6, 8, 24 and 48 hours after the first dose and pre-dose, 0.5, 1, 2, and 3 hours after the second dose. ECG should be collected at follow-up for all groups.
[7] Urine will be collected for PK and metabolite characterization on Day 1 pre-dose, cumulatively from 0-12, 12-24, and 24-48 hours post-dose. Total volume to be collected. Please see Laboratory Manual for further details. For Group 5, time points are based on the first dose.
[8] All female participants will be tested for pregnancy at screening (serum) and Day −1 (urine or serum).
[9] Post-menopausal female participants only if less than 12 months after last menstrual period.
[10] Prior to dosing.
[11] Blood will be collected for PK on Day 1 pre-dose and 0.5, 1, 2, 3, 4, 6, 8, 12, 24, and 48 hours post-dose for Groups 1 to 4. For Group 5 (every 12 hour dosing), blood for PK should be collected on Day 1 pre-dose, 0.5, 1, 2, 3, 4, 5, 6, 8, 24, and 48 hours after the first dose and pre-dose, 0.5, 1, 2, and 3 hours after the second dose.
[12] Blood will be collected for PD on Day 1 pre-dose, and 2 and 24 hours post-dose. For Group 5, time points are based on the first dose.
[13] Telemetry will be performed from 30 minutes pre-dose to 24 hours post-dose on Day 1. For Group 5, time points are based on the first dose.
[14] Adverse events will be collected from informed consent through follow-up.
[15] To be performed 4-7 days after discharge or early discontinuation.
DSST: Digit Symbol Substitution Test;
ECG: electrocardiogram;
EEG: electroencephalogram;
FSH: follicle-stimulating hormone;
PD: pharmacodynamics;
PK: pharmacokinetics;
VAS: Visual Analog Scale

TABLE 2

Schedule of Assessments—Multiple Ascending Dose

| Visit | Screening | Admission | Confinement | | | | Discharge | Follow-up |
|---|---|---|---|---|---|---|---|---|
| Study Day | −28 to −2 | −1 | 1 | 2 | 3 | 4 | 5 | 9 to 12 [14] |
| Written informed consent | X | | | | | | | |
| Medical history | X | | | | | | | |
| Medical history update | | X | | | | | | X |
| Physical examination [1] | X | X | X | X | X | | | X |
| Neurological examination [2] | X | X | X | X | X | X | X | X |
| VAS/DSST [3] | | X | X | X | X | X | X | |
| EEG [4] | X | | | | | | | |
| Vital signs [5] | X | X | X | X | X | X | X | X |

TABLE 2-continued

Schedule of Assessments—Multiple Ascending Dose

| Visit | Screening | Admission | Confinement | | | | Discharge | Follow-up |
|---|---|---|---|---|---|---|---|---|
| Study Day | −28 to −2 | −1 | 1 | 2 | 3 | 4 | 5 | 9 to 12 [14] |
| 12-lead ECG [6] | X | X | X | X | X | X | X | X |
| Viral serology | X | | | | | | | |
| ETOH and drug screen | X | X | | | | | | |
| Hematology | X | X | | X | | X | X | X |
| Chemistry | X | X | | X | | X | X | X |
| Coagulation | X | X | | X | | X | X | X |
| Urinalysis | X | X | | X | | X | X | X |
| Serum pregnancy test [7] | X | | | | | | | |
| Urine pregnancy test [7] | | X | | | | | | |
| Hormone panel (FSH testing) [8] | X | | | | | | | |
| Eligibility criteria review | X | X [9] | | | | | | |
| Randomisation | | | X | | | | | |
| PK blood draw [10] | | | X | X | X | X | X | X |
| PD blood draw [11] | | | X | | X | X | | |
| Telemetry [12] | | | X | X | | | | |
| Study drug administration | | | X | X | X | X | | |
| Adverse event monitoring [13] | X | X | X | X | X | X | X | X |

Table 2 notes:
[1] A complete physical examination will be performed at screening (height and weight included at screening only). A physical examination update will be performed on Days 1, 2, and 3, and at follow-up.
[2] Neurological examination consists of a clinical evaluation and Body Sway test. A full neurological examination will be performed at screening, Day −1, and at follow-up. An abbreviated exam consisting of a clinical examination (targeted), Body Sway test, and indication-specific examination will be performed on all other days.
[3] Bond and Lader VAS of Mood and Alertness; DSST; training DSST and first test on Day −1, on Days 1, 2, 3, 4, and 5 DSST test in time window of 2-4 hours post-dose for Groups 1 to 4, and on Day 1 in time window of 2-4 hours after the morning dose for Group 5.
[4] EEG will be performed at screening for participants receiving doses higher than 75 mg (ie, Groups 3 and higher) and if clinically indicated for any neurological adverse events during the study.
[5] Vital signs consist of blood pressure, pulse rate, body temperature, and respiratory rate. Supine and standing vital signs are to be performed in triplicate at screening and Day −1. Single supine and standing vital signs will be collected on Day 1 to Day 4 pre-dose and 1, 2, 3, 4, 6, 8, 12, hours post-dose for Groups 1-4. For Group 5 (every 12 hour dosing), vital signs will be collected on Day 1 to Day 4 pre-dose and 1, 2, 3, 4, 6, 8 hours after first dose and pre-dose, 1, 2, and 3 hours after second dose. On Day 5, vital signs will be collected prior to discharge, and at follow-up for all groups.
[6] ECG will be collected in triplicate at all time points. Participants should be least 15 minutes in supine position before each triplicate ECG. ECGs should be collected before each PK sample if PK sample is at the same timepoint. ECGs will be collected at screening, Day −1 on admission. ECGs will be collected on Day 1 and Day 4 pre-dose and 0.5, 1, 2, 3, 4, 6, 8, and 12 hours post-dose, Day 2 and Day 3 pre-dose only for Groups 1 and 4. For Group 5 (every 12 hours dosing), ECG should be collected on Day 1 to Day 4 pre-dose, 0.5, 1, 2, 3, 4, 6, 8 hours after the first dose and pre-dose, 1, 2, and 3 hours after the second dose. On Day 5, ECG will be collected prior to discharge, and at follow-up for all groups. All groups will have ECG done on Day 5 at 8:00 am (±15 minutes) and at follow-up.
[7] All female participants will be tested for pregnancy at screening (serum) and Day −1 (urine or serum).
[8] Post-menopausal female participants only if less than 12 months after last menstrual period.
[9] Prior to dosing.
[10] Blood will be collected for PK on Day 1 and Day 4 pre-dose and 0.5, 1, 2, 3, 4, 6, 8, and 12 hours post-dose, Day 2 and Day 3 pre-dose only for Groups 1 to 4. For Group 5 (every 12 hour dosing), blood for will be collected for PK on Day 1 and Day 4 pre-dose, 0.5, 1, 2, 3, 4, 6, 8 hours after the first dose and pre-dose, 1, 2, and 3 hours after second dose. For Group 5, Day 2 and Day 3 pre-dose before the morning and evening dose. All groups will have blood collected for PK on Day 5 at 8:00 am (±15 minutes).
[11] Blood will be collected for PD on Day 1 pre-dose and Day 4 pre-dose, and 2 and 24 hours post-dose. For Group 5, time points are based on the first dose.
[12] Telemetry will be performed from 30 minutes pre-dose to 24 hours post-dose on Day 1. For Group 5, time points are based on the first dose.
[13] Adverse events will be collected from informed consent through follow-up.
[14] To be performed 4-7 days after discharge or early discontinuation.
DSST: Digit Symbol Substitution Test;
ECG: electrocardiogram;
EEG: electroencephalogram;
FSH: follicle-stimulating hormone;
PD: pharmacodynamics;
PK: pharmacokinetics;
VAS: Visual Analog Scale

TABLE 3

Schedule of Assessments—Food Effect (fed and fasting)

| | Study Period | | | | | | | | |
|---|---|---|---|---|---|---|---|---|---|
| | Period 1 | | | | | Period 2 | | | |
| Visit | Screening | Admission | Confinement | Discharge | Wash-out | Admission | Confinement | Discharge | Follow-up |
| Study Day | −28 to −2 | −1 | 1 | 2 | 3 | 4 to 5 | 6 | 7 | 8 | 9 | 13 to 16 [13] |
| Written informed consent | X | | | | | | | | | |
| Medical history | X | | | | | | | | | |
| Medical history update | | X | | | | | | | | X |
| Physical examination [1] | X | X | X | X | X | | X | X | X | X |
| Neurological examination [2] | X | X | X | X | X | | X | X | X | X |

TABLE 3-continued

Schedule of Assessments—Food Effect (fed and fasting)

| Visit | Screening | Period 1 | | | | Wash-out | Period 2 | | | | Follow-up |
|---|---|---|---|---|---|---|---|---|---|---|---|
| | | Admission | Confinement | | Discharge | | Admission | Confinement | | Discharge | |
| Study Day | −28 to −2 | −1 | 1 | 2 | 3 | 4 to 5 | 6 | 7 | 8 | 9 | 13 to 16 [13] |
| VAS/DSST [3] | | X | X | X | | | X | X | X | | |
| EEG [4] | X | | | | | | | | | | |
| Vital signs [5] | X | X | X | X | X | | X | X | X | X | X |
| 12-lead ECG [6] | X | X | X | X | | | X | X | X | | X |
| Viral serology | X | | | | | | | | | | |
| ETOH and drug screen | X | X | | | | | X | | | | |
| Hematology | X | X | | | X | | X | | | X | X |
| Chemistry | X | X | | | X | | X | | | X | X |
| Coagulation | X | X | | | X | | X | | | X | X |
| Urinalysis | X | X | | | X | | X | | | X | X |
| Serum pregnancy test [7] | X | | | | | | | | | | |
| Urine or serum pregnancy test [7] | | X | | | | | X | | | | |
| Hormone panel (FSH testing) [8] | X | | | | | | | | | | |
| Eligibility criteria review | X | X [9] | | | | | | | | | |
| Randomisation | | | X | | | | | | | | |
| PK blood draw [10] | | | X | X | X | | | X | X | X | |
| Telemetry [11] | | | X | X | | | | X | X | | |
| Study drug administration | | | X | | | | | X | | | |
| Adverse event monitoring [12] | X | X | X | X | X | X | X | X | X | X | X |

Table 3 notes:
[1] A complete physical examination will be performed at screening (height and weight included at screening only). A physical examination update will be performed on all other in-house days, and at follow-up.
[2] Neurological examination consists of a clinical evaluation and Body Sway test. A full neurological examination will be performed at screening, Days −1 and 6, and at follow-up. An abbreviated exam consisting of a clinical examination (targeted). Body Sway test, and indication-specific examination will be performed on all other days.
[3] Bond and Lader VAS of Mood and Alertness; DSST; training DSST and first test on Day −1 and Day 6, on Days 1, 2, 7, and 8 DSST test in time window of 2-4 hours post-dose.
[4] EEG will be performed at screening for participants receiving doses higher than 75 mg (ie, Groups 3 and higher). Subjects in the FE part will have an EEG at baseline and if clinically indicated for any neurological adverse events during the study.
[5] Vital signs consist of blood pressure, pulse rate, body temperature, and respiratory rate. Supine and standing vital signs are to be performed in triplicate at screening and Day −1 and Day 6. Single supine and standing vital signs will be collected on Day 1 and Day 7 pre-dose and 1, 2, 3, 4, 6, 8, 12, 24, and 48 hours post-dose and at follow-up.
[6] ECG will be collected in triplicate at all time points. Participants should be least 15 minutes in supine position before each triplicate ECG. ECGs should be done before each PK sample if PK sample is at the same timepoint. ECGs will be collected at screening, Day −1 and Day 6 at admission and 2, 4, and 6 hours after admission. ECGs will be collected pre-dose and 0.5, 1, 2, 3, 4, 6, 8, 12, 24 and 48 hours post last dose on Day 1 and Day 7 (and other days if clinically indicated), and at follow-up.
[7] All female participants will be tested for pregnancy at screening (serum) and Day −1 and Day 6 (urine or serum).
[8] Post-menopausal female participants only if less than 12 months after last menstrual period.
[9] Prior to dosing.
[10] Blood will be collected for PK pre-dose and 0.5, 1, 2, 3, 4, 6, 8, 12, 24, and 48 hours post-dose on Day 1 and Day 7.
[11] Telemetry will be performed from 30 minutes pre-dose to 24 hours post-dose on Day 1 and Day 7.
[12] Adverse events will be collected from informed consent through follow-up.
[13] To be performed 4-7 days after discharge or early discontinuation.
DSST: Digit Symbol Substitution Test;
ECG: electrocardiogram;
EEG: electroencephalogram;
FSH: follicle-stimulating hormone;
PD: pharmacodynamics;
PK: pharmacokinetics;
VAS: Visual Analog Scale The timing of assessments may be changed based on data from initial groups. Based on emerging data, less, or up to 3 additional assessments may be performed for all participants while not changing the duration of stay, changing the number of visits or exceeding the maximum allowed volume of blood drawn in this study. Additional assessments, including specialist referrals, may be performed if it is considered clinically necessary by the Investigator for individuals on a case-by-case basis.

Blood and Urine Sampling

At the time points defined in the schedule(s) of assessments, blood samples of 3 mL each will be taken for the analysis of Compound I in plasma samples. The blood samples will be taken via an indwelling IV catheter or by direct venipuncture into specified tubes.

Pharmacodynamic Measurements

The assessment of pCREB (a marker for $A_2R$ inhibition) by flow cytometry will be conducted during the study. Blood samples were collected from trial subjects at time points corresponding to pre-dose, 2 hours post dose, and 24 hours post dose, incubated with 5 μM NECA (a synthetic adenosine analogue) ex vivo and analyzed.

Safety and Tolerability Measurements

Safety and tolerability assessments will consist of adverse events (AEs), clinical laboratory, vital signs, 12-lead ECG, telemetry, physical examination, Bond and Lader Visual Analog Scale (VAS) of Mood and Alertness, and Digit Symbol Substitution Test (DSST). Assessments will be performed in accordance with the schedules of assessments.

PK Summary for SAD Cohorts

Compound I has been administered in doses of up to 150 mg in healthy volunteers and no safety issues have been identified. FIG. 1 shows that increased doses of Compound I resulted in dose proportional increases in plasma levels of Compound I. The plasma half life of Compound I following a single dose is approximately 20 hours.

Figure 2:
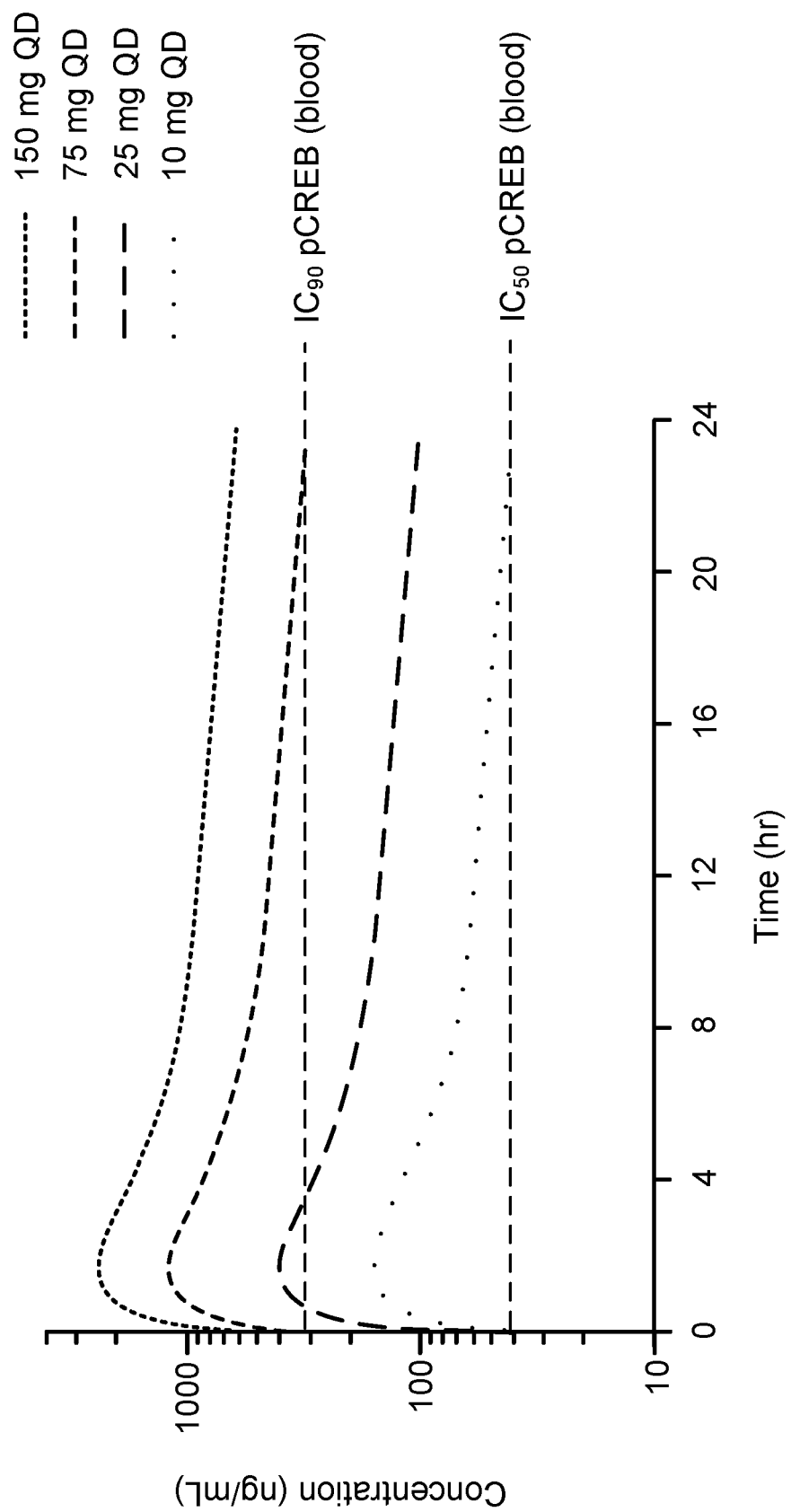
FIG. 2 describes the expected steady-state plasma levels of Compound I based on the pharmacokinetic parameters obtained from the single-dose pharmacokinetic profiles.

FIG. 2 describes the expected steady-state plasma levels of Compound I based on the pharmacokinetic parameters obtained from the single-dose pharmacokinetic profiles.

According to these profiles, 75 mg of Compound I once daily should be sufficient to inhibit 90% of $A_2R$ in the presence of 5 µM of NECA.

Figure 3:
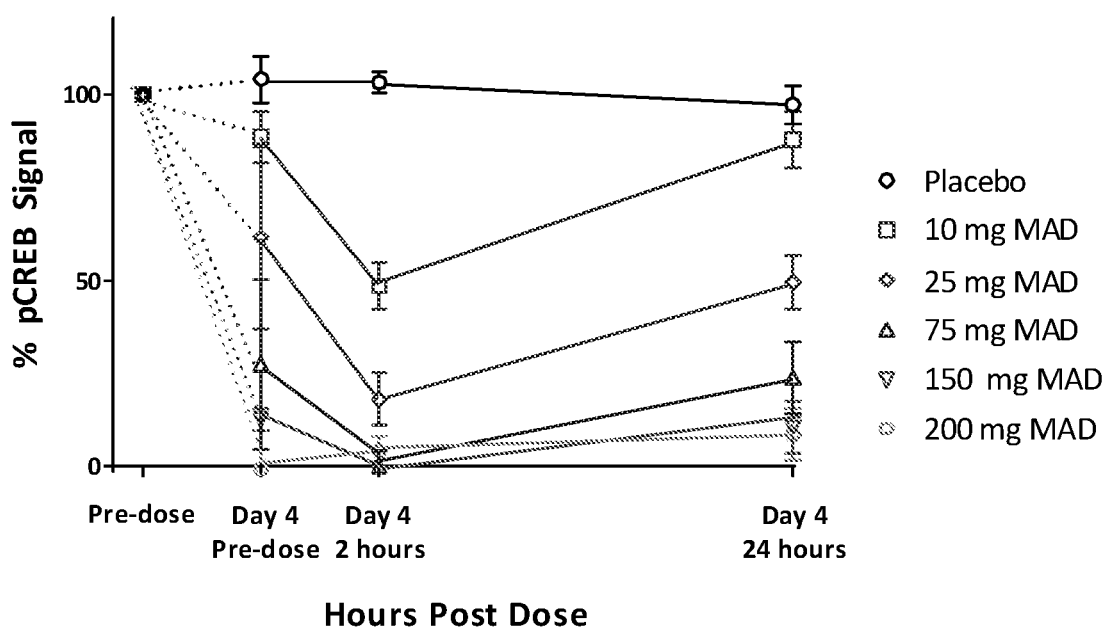
FIG. 3 describes the mean pCREB activation signal for the pooled placebo group (6 subjects) and for each healthy volunteers group in the multiple ascending portion of the study (6 subjects per group) over the timepoints indicated.

FIG. 3 shows the mean inhibition of pCREB activation for the pooled placebo group (6 subjects) and 6 subjects receiving 150 mg of Compound I. Prior to dosing, all subjects responded to 5 µM NECA by increasing the levels of pCREB in their blood CD8+ T cells. At two hours after dosing, the placebo group maintained their pCREB activation signal in response to NECA stimulation while the active group had no detectable increase in pCREB levels, demonstrating Compound I's ability to block the activation of $A_{2a}R$ by NECA. Twenty-four hours after dosing, the placebo group maintained a response similar to their pre-dose level, while the active group only showed approximately 10% of the response seen pre-dose, indicating that the levels of Compound I remaining at 24 hours were still sufficient to inhibit approximately 90% of the NECA-mediated activation of $A_{2a}R$.

Example 3: Phase I Studies to Evaluate the Safety and Tolerability of Immunotherapy Combinations in Participants with Advanced Malignancies Compound I is being evaluated in several Phase I, open-label, dose-escalation studies to assess its safety and tolerability when given in combination to participants with various solid tumors. The various solid tumors may include non-small cell lung cancer, squamous cell carcinoma of the head and neck, breast cancer, colorectal cancer, melanoma, bladder cancer, ovarian cancer, endometrial cancer, Merkel cell carcinoma, gastroesophageal cancer or renal cell carcinoma.

Generally, the Phase I studies will evaluate increasing dose levels of Compound I (75, 150, and 200 mg orally QD) in combination with a fixed dose of a therapeutic partner in participants with various solid tumor types. Participants will be assigned to a dose cohort in the order of study entry.

Based on a 3+3 design, the dose escalation for each Phase I study will be initiated with 3 participants enrolled in the initial dose cohort. Participants will continue to receive Compound I until disease progression or toxicity as assessed by the investigator. Three to 6 participants will be treated at each dose level. When a minimum of 3 participants who are evaluable for toxicity have completed the DLT evaluation period, subsequent participants may be enrolled at the same dose level, a lower dose level, a higher dose level, or a dose may be chosen as the recommended Phase 2 dose provided it has not exceeded the maximum tolerated dose (MTD).

The planned sample size for dose escalation for each Phase I study includes up to 18 participants, depending on the toxicities observed. More participants may be enrolled to explore other doses. The safety analysis will be based on the as-treated population, which comprises all participants who receive at least 1 dose of Compound I. The efficacy analysis will be based on the intent-to-treat population, which comprises all participants who are enrolled and assigned to receive Compound I.

Inclusion Criteria

Generally, the following inclusion criteria must be met for a participant to be eligible in the studies:
1. Male or female participants ≥18 years
2. Pathologically confirmed non-small cell lung cancer, squamous cell carcinoma of the head and neck, renal cell carcinoma, breast cancer, colorectal cancer, melanoma, bladder cancer, ovarian cancer, endometrial cancer, Merkel cell carcinoma, or gastroesophageal cancer that is metastatic, advanced or recurrent with progression for which no alternative or curative therapy exists or standard therapy is not considered appropriate by the participant and treating physician (reason must be documented in medical records).
3. Must have at least 1 measurable lesion per RECIST v1.1.
4. Eastern Cooperative Oncology Group (ECOG) performance status score of 0 or 1.
5. Must have received standard of care, including potentially curative available therapies or interventions.
6. Confirm that an archival tissue sample is available and ≤6 months old; if not, a new biopsy of a tumor lesion must be obtained.
7. Adequate organ and marrow function Exclusion Criteria Generally, a participant who meets any of the following criteria will not be eligible for the studies:
1. Use of any live vaccines against infectious diseases (eg, influenza, varicella) within 4 weeks (28 days) of initiation of Compound I.
2. Underlying medical conditions that will make the administration of Compound I hazardous (eg, interstitial lung disease, active infections requiring antibiotics, recent hospitalization with unresolved symptoms) or obscure the interpretation of toxicity determination or AEs, or concurrent medical condition requiring the use of immunosuppressive medications or immunosuppressive doses of systemic or absorbable topical corticosteroids.
3. Has known psychiatric or substance abuse disorders that would interfere with cooperation with the requirements of the trial.
4. Is pregnant or breastfeeding or expecting to conceive or father children within the projected duration of the study, starting with the pre-screening or screening visit through 90 days after the last dose of Compound I.
5. Any active autoimmune disease or a documented history of autoimmune disease that required systemic treatment in past 2 years, except for vitiligo or resolved childhood asthma/atopy. Participants with asthma who require intermittent use of bronchodilators (such as albuterol) will not be excluded from this study.
6. Prior malignancy active within the previous year except for locally curable cancers that have been apparently cured, such as basal or squamous cell skin cancer, superficial bladder cancer or carcinoma in situ of the cervix, breast, or prostate cancer.
7. Has had prior chemotherapy, targeted small-molecule therapy, or radiation therapy within 2 weeks prior to Day 1 or has not recovered (ie, ≤Grade 1 or baseline) from AEs due to a previously administered agent, except ≤Grade 2 alopecia or ≤Grade 2 neuropathy.
8. Use of other investigational drugs (drugs not marketed for any indication) within 28 days before administration of Compound I.

Efficacy Assessments

Participants will undergo tumor assessments, regardless of dose delays, until loss of clinical benefit as determined by the investigator. All participants who discontinue Compound I for reasons other than disease progression (eg. AEs) will continue tumor assessments until death, disease progression, initiation of another systemic anticancer therapy, lost to follow-up, withdrawal of consent, or study termination, whichever occurs first. At the investigator's discretion, tumor assessments may be repeated at any time if progressive disease is suspected.

All measurable and evaluable lesions should be reassessed at each subsequent tumor evaluation. The same radiographic procedures used to assess disease sites at screening should be used for subsequent tumor assessments (eg, same contrast protocol for CT scans).

Response will be assessed by the Investigator using RECIST v1.1. Assessments should be performed by the same evaluator, if possible, to ensure internal consistency across visits. Results must be reviewed by the investigator before dosing at the next cycle.

Safety Assessments

Safety assessments will consist of monitoring and recording of AEs, including SAEs, performing safety laboratory assessments, measuring vital signs, and conducting other protocol-specified tests that are deemed critical to the safety evaluation of the study.

Preliminary Results

Figure 4:
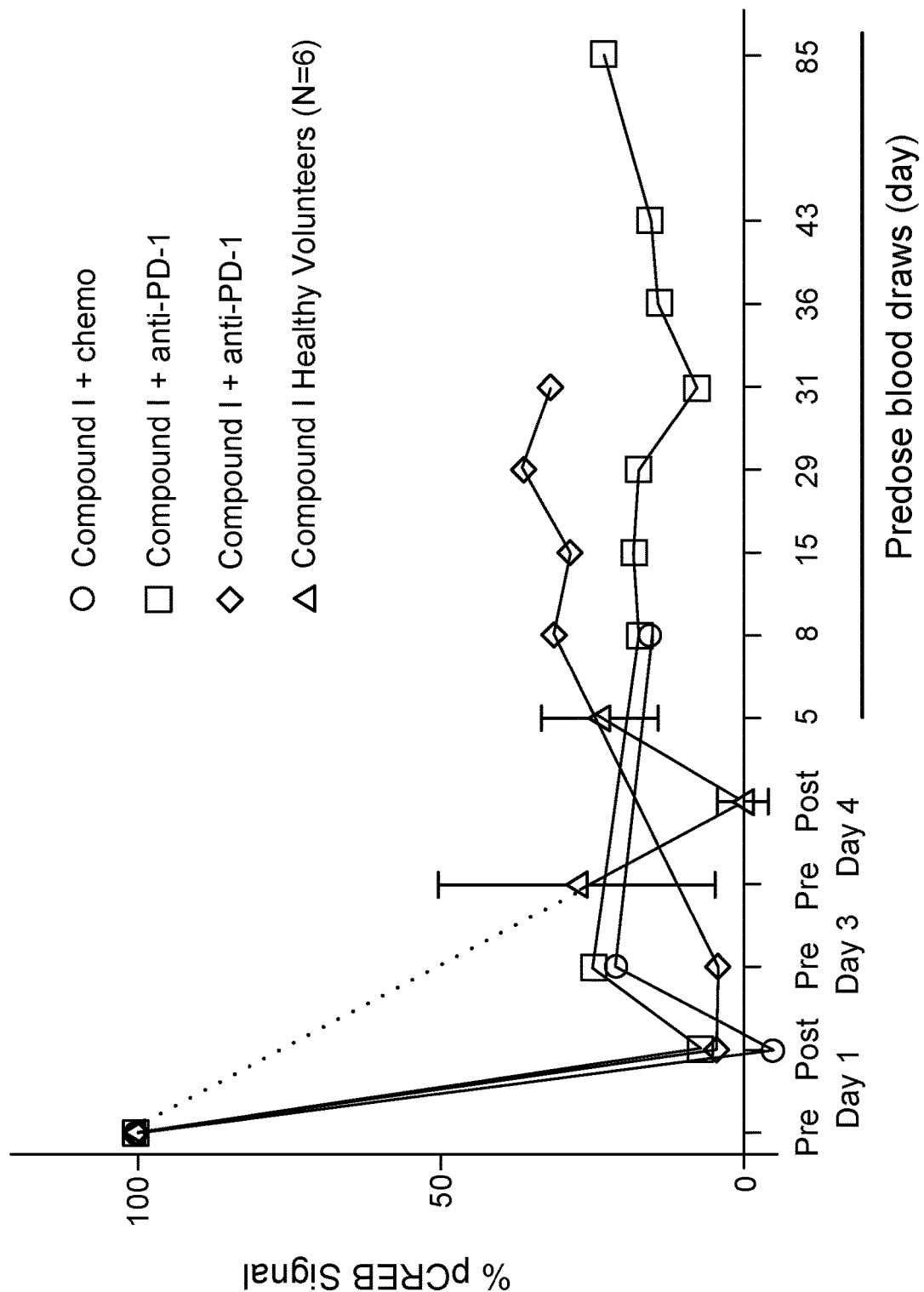
FIG. 4 shows the percent inhibition of pCREB from both healthy and oncology subjects receiving 75 mg of Compound I.

Preliminary results demonstrate that the PK and PD profile of Compound I in oncology subjects is consistent with that in healthy volunteer subjects. FIG. 4 shows the percent inhibition of pCREB from both healthy and oncology subjects receiving 75 mg of Compound I.

Particular embodiments of this invention are described herein, including the best mode known to the inventors for carrying out the invention. Upon reading the foregoing, description, variations of the disclosed embodiments may become apparent to individuals working in the art, and it is expected that those skilled artisans may employ such variations as appropriate. Accordingly, it is intended that the invention be practiced otherwise than as specifically described herein, and that the invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All publications, patent applications, accession numbers, and other references cited in this specification are herein incorporated by reference as if each individual publication or patent application were specifically and individually indicated to be incorporated by reference.

What is claimed is:

1. A method of treating a disease, disorder, or condition, mediated at least in part by adenosine $A_{2A}$ receptor ($A_{2A}R$), at least in part by adenosine $A_{2B}$ receptor ($A_{2B}R$), or at least in part by both $A_{2A}R$ and $A_{2B}R$ receptors, said method comprising administering to a subject in need thereof a total daily dosage of about 5 to 250 mg of Compound I, having the formula:

(Compound I)

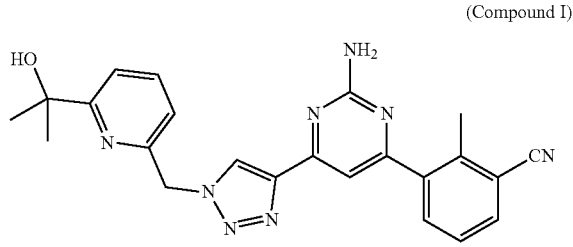 [SMILES: Cc1c(C#N)cccc1-c1cc(-c2cn(Cc3cccc(C(C)(C)O)n3)nn2)nc(N)n1]

or a pharmaceutically acceptable salt thereof.

2. The method of claim 1, wherein said total daily dosage is about 100 mg per day.

3. The method of claim 1, wherein said total daily dosage is about 75 mg per day.

4. The method of claim 1, wherein said total daily dosage is from about 75 to 150 mg per day.

5. The method of claim 1, wherein said total daily dosage is from about 125 to 150 mg per day.

6. The method of claim 1, wherein said total daily dosage is about 150 mg per day.

7. The method of claim 1, wherein said Compound I is administered orally.

8. The method of claim 1, wherein said Compound I is administered once daily.

9. The method of claim 1, wherein said disease, disorder, or condition is mediated at least in part by both $A_{2A}R$ and $A_{2B}R$ receptors.

10. The method of claim 1, wherein said disease, disorder, or condition is cancer.

11. The method of claim 10, wherein said cancer is a cancer of the prostate, colon, rectum, pancreas, cervix, stomach, endometrium, brain, liver, bladder, ovary, testis, head, neck, skin, mesothelial lining, white blood cell, esophagus, breast, muscle, connective tissue, lung, adrenal gland, thyroid, kidney, or bone; or is glioblastoma, mesothelioma, renal cell carcinoma, gastric carcinoma, sarcoma, choriocarcinoma, cutaneous basocellular carcinoma, or testicular seminoma.

12. The method of claim 10, wherein said cancer is triple-negative breast cancer.

13. The method of claim 10, wherein said cancer is non-small-cell lung carcinoma.

14. The method of claim 10, wherein said cancer is colorectal cancer.

15. The method of claim 10, wherein said cancer is pancreatic cancer.

16. The method of claim 10, wherein said cancer is prostate cancer.

17. The method of claim 10, wherein said cancer is ovarian cancer.

18. A method of treating cancer in a subject, said method comprising administering to said subject a total daily dosage of about 5 to 250 mg of Compound I, having the formula:

(Compound I)

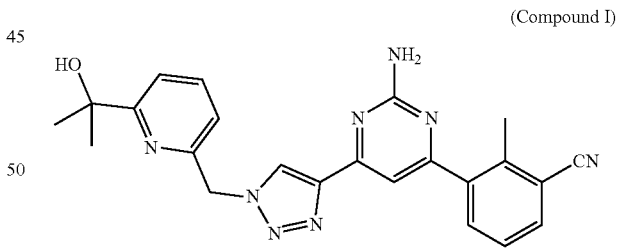

or a pharmaceutically acceptable salt thereof and at least one additional therapeutic agent.

19. The method of claim 18, wherein said at least one additional therapeutic agent is a chemotherapeutic agent.

20. The method of claim 18, wherein said at least one additional therapeutic agent blocks the activity of at least one of PD-1, PD-L1, TIGIT, or CTLA-4.

21. The method of claim 20, further comprising administering to said subject a chemotherapeutic agent.

22. The method of claim 19, wherein said chemotherapeutic agent is oxaliplatin or doxorubicin.

23. The method of claim 19, wherein said chemotherapeutic agent is fluorouracil.

24. A pharmaceutical composition comprising about 5 to 250 mg of Compound I, having the formula:
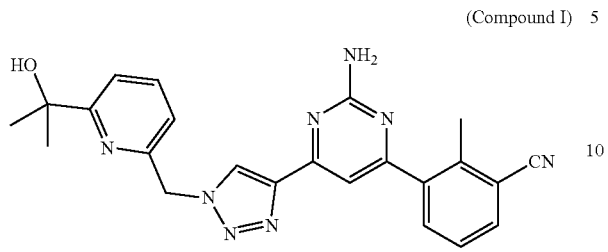
(Compound I)
or a pharmaceutically acceptable salt thereof, and a pharmaceutically acceptable excipient.
25. A single unit dosage capsule or tablet form comprising about 5 to 250 mg of Compound I, having the formula:
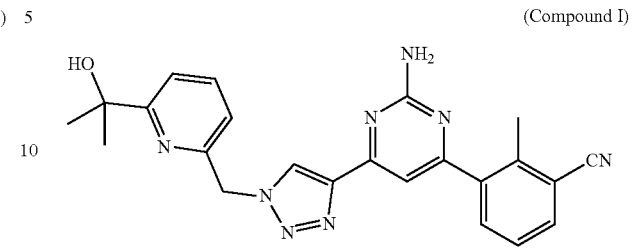
(Compound I)
or a pharmaceutically acceptable salt thereof.
* * * * *